(12) United States Patent
Mansouri et al.

(10) Patent No.: US 7,022,219 B2
(45) Date of Patent: Apr. 4, 2006

(54) AUTOMATED SYSTEM FOR CONTINUOUSLY AND AUTOMATICALLY CALIBRATING ELECTROCHEMICAL SENSORS

(75) Inventors: Sohrab Mansouri, Sudbury, MA (US); Kevin Fallon, East Falmouth, MA (US); Patti Eames, Groton, MA (US)

(73) Assignee: Instrumentation Laboratory Company, Lexington, MA (US)

( * ) Notice: Subject to any disclaimer, the term of this patent is extended or adjusted under 35 U.S.C. 154(b) by 227 days.

(21) Appl. No.: 10/227,618

(22) Filed: Aug. 22, 2002

(65) Prior Publication Data

US 2003/0062262 A1    Apr. 3, 2003

Related U.S. Application Data

(60) Provisional application No. 60/314,267, filed on Aug. 22, 2001.

(51) Int. Cl.
G01N 27/327 (2006.01)

(52) U.S. Cl. .................. 205/792; 205/775; 204/401; 204/403.01

(58) Field of Classification Search ........... 204/401, 204/403, 406–409, 411, 412, 433; 436/8, 436/14–16, 18, 52, 55, 66, 68; 422/68.1, 422/81, 62, 82.01, 82.02, 105, 108; 600/373; 205/778, 775, 792; 604/93.01
See application file for complete search history.

(56) References Cited

U.S. PATENT DOCUMENTS

| | | | |
|---|---|---|---|
| 3,874,850 A * | 4/1975 | Sorensen et al. | 436/50 |
| 3,960,497 A * | 6/1976 | Acord | 422/67 |
| 4,271,474 A | 6/1981 | Belanger et al. | 364/500 |
| 4,481,804 A | 11/1984 | Eberhard et al. | 73/1 |
| 4,734,184 A * | 3/1988 | Burleigh et al. | 204/409 |
| 4,787,398 A * | 11/1988 | Garcia et al. | 600/583 |
| 4,975,647 A | 12/1990 | Downer et al. | 324/425 |
| 5,022,980 A * | 6/1991 | Tanaka et al. | 204/400 |
| 5,061,631 A | 10/1991 | Calabrese | 436/11 |
| 5,067,093 A | 11/1991 | Przybylowicz et al. | 364/498 |
| 5,070,023 A | 12/1991 | Calabrese et al. | 436/8 |
| 5,103,179 A | 4/1992 | Thomas et al. | 324/438 |
| 5,112,454 A | 5/1992 | Tanaka et al. | 204/153.1 |
| 5,198,093 A | 3/1993 | Sydlowski et al. | 204/405 |
| 5,766,432 A * | 6/1998 | Dunn et al. | 204/412 |
| 5,966,676 A | 10/1999 | Fujiwara et al. | 702/85 |
| 5,976,085 A | 11/1999 | Kimball et al. | 600/309 |
| 6,088,608 A * | 7/2000 | Schulman et al. | 600/345 |
| 6,123,827 A * | 9/2000 | Wong et al. | 205/775 |
| 6,136,607 A * | 10/2000 | Conlon et al. | 436/8 |

(Continued)

FOREIGN PATENT DOCUMENTS

DE    32 20 327 A1    12/1982

(Continued)

OTHER PUBLICATIONS

42 CFR 493.1213, 1215, 1217, 1218, dated Oct. 1, 2002.*

(Continued)

*Primary Examiner*—Alex Noguerola
(74) *Attorney, Agent, or Firm*—Kirkpatrick & Lockhart Nicholson Graham LLP

(57) ABSTRACT

An electrochemical sensor system that continuously monitors and calibrates the sensors included in the system. The invention also includes a method for determining failure patterns of a sensor and incorporating into an electrochemical sensor system the ability to recognize the failure pattern and initiate remedial action.

34 Claims, 9 Drawing Sheets

U.S. PATENT DOCUMENTS 6,512,986 B1 * 1/2003 Harmon .................... 702/84
6,554,788 B1 * 4/2003 Hunley et al. ............ 604/4.01

FOREIGN PATENT DOCUMENTS

| DE | 195 46 535 A1 | 6/1997 |
| WO | 98/32013 | 7/1998 |
| WO | 01/42473 A2 | 6/2001 |

OTHER PUBLICATIONS

Patent Cooperation Treaty, International Search Report, International Application No. PCT/US02/26851, mailed on Jul. 11, 2003, 7 pages.

Patent Cooperation Treaty, Written Opinion, International Application No. PCT/US02/26851, mailed on Aug. 25, 2003, 7 pages.

* cited by examiner

| Analyzer | | S/N | | Name | | | Other Months | Print | Exit |

Month

07/21/2002 23:30:03 Cartridge Lot No.: [1]
Cartridge Removed.
Samples Remaining = 412
No. of Solution B Adjustments = 6

07/20/2002 07:00:39 Cartridge Lot No.: [2]
Interference Detected After Sample#
Operator:
Operator Notified. Sensor Output Adjusted.
Cleared 07/20/2002 06:44:05 Cartridge Lot No.: [3]
CVP Error for Hct. Operator:
Repeated CVP
Corrected 07/17/2002 23:17:41 Cartridge Lot No.: [4]
Micro Clot Caused Solution Detect Error After Sample #
Operator:
Operator Notified.
Fluidics Checked.
Corrected

AUTOMATED SYSTEM FOR CONTINUOUSLY AND AUTOMATICALLY CALIBRATING ELECTROCHEMICAL SENSORS

CROSS-REFERENCE TO RELATED APPLICATIONS

This application claims priority to U.S. provisional patent application Ser. No. 60/314,267, filed Aug. 22, 2001.

FIELD OF THE INVENTION

The present invention is related to the field of electrochemical sensors, particularly to the increased accuracy of electrochemical sensors used to measure analytes in body fluids.

BACKGROUND OF THE INVENTION

In a variety of clinical situations, it is important to measure certain chemical characteristics of the patient's blood, such as pH, hematocrit, the ion concentration of calcium, potassium, chloride, sodium, glucose, lactate, creatinine, creatine, urea, the partial pressure of $O_2$, and/or $CO_2$, and the like. These situations range from a routine visit of a patient to a physician's office to the monitoring of a patient during open-heart surgery. Further, the required speed, accuracy, and other performance characteristics of such measurements vary with each situation.

Electrochemical sensor systems such as those described in U.S. Ser. No. 09/549,968, U.S. Ser. No. 09/872,247, U.S. Ser. No. 09/871,885, and U.S. Ser. No. 09/872,240, the entire disclosure of each incorporated by reference herein, are typically used to provide this blood-chemistry analysis on a patient's blood. Conventional sensor systems are either stand-alone machines or machines that connect to an extracorporeal shunt. Alternatively, these sensors can also connect to an ex vivo blood source, such as a heart/lung machine. To obtain a blood sample from a heart/lung machine, for example, small test samples of blood can be diverted off-line from either the venous or arterial flow lines of the heart/lung machine to a bank of micro-electrodes of the electrochemical sensor system.

Conventional micro-electrodes generate electrical signals proportional to chemical characteristics of the blood sample. To generate these electrical signals, the sensor systems may combine a chemical or biochemical recognition component (e.g., an enzyme) with a physical transducer such as a platinum electrode. Traditional chemical or biochemical recognition components selectively interact with an analyte of interest to generate, directly or indirectly, the needed electrical signal through the transducer.

The selectivity of certain biochemical recognition components makes it possible for electrochemical sensors to accurately detect certain biological analytes, even in a complex analyte mixture such as blood. Despite the high degree of selectivity of these sensors, the accuracy of such sensors depends on keeping the sensors calibrated at all times. One technique used to monitor sensor calibration is to manually verify the calibration of the sensor using an external verification solution. This technique, however, is often labor-intensive, as it is typically performed several times a day. Further, the delay between the manual verifications of the sensor may prevent a timely discovery of an uncalibrated sensor.

Another method used to monitor sensor calibration is to monitor the sensor with an external verification solution automatically at set time intervals, such as every 8 hours. Although not as labor-intensive as manually verifying a sensor, this technique may instead make it difficult to detect errors in a timely fashion, thereby enabling inaccurate readings from the sensor if it becomes uncalibrated before the scheduled verification (and correction) time. Further, automatic monitoring methods may not detect a small fraction of uncalibrated sensors. This gap in sensitivity of the automatic monitoring methods may result in uncalibrated sensors not receiving the needed corrective actions.

SUMMARY OF THE INVENTION

One objective of the present invention is to provide a system and method for the automatic and continuous monitoring of an electrochemical sensor system. The system of the present invention maintains the calibration of all electrochemical sensors in the electrochemical sensor system automatically at all times without the scheduled involvement of an operator. The system of the present invention further recognizes and is capable of correcting failures in the calibration of a sensor that are typically not recognized by standard monitoring methods.

In one aspect of the present invention, a method for automatic monitoring of an electrochemical sensor system includes providing an electrochemical sensor system including at least one electrochemical sensor. The method includes analyzing an analyte that includes a known concentration in a first reference solution to determine a first measurement of the known concentration of the analyte. The method also includes analyzing the analyte in the first reference solution to determine a second measurement of the known concentration of the analyte. The method additionally includes comparing the known concentration, first measurement of the known concentration and second measurement of the known concentration of the analyte. In yet another step, the method includes automatically initiating corrective action if the first measurement of the analyte is substantially similar to the second measurement of the analyte and the first and second measurements are substantially dissimilar to the known concentration of the analyte.

In one embodiment, the corrective action includes calibrating the electrochemical sensor according to the known concentration of the analyte of the reference solution. The corrective action may also include rinsing the electrochemical sensor. In yet another embodiment, the electrochemical sensor system includes a sample flow channel disposed adjacent to the electrochemical sensor.

In another aspect of the invention, a method for automatic monitoring of an electrochemical sensor system for measuring an analyte in a fluid sample includes providing an electrochemical sensor system including at least one electrochemical sensor. The method also includes analyzing an analyte including a known concentration in a first reference solution to determine a first measurement of the known concentration of the analyte, and analyzing the analyte in the first reference solution to determine a second measurement of the known concentration of the analyte. The method additionally compares the known concentration, first measurement of the known concentration and second measurement of the known concentration. The method also measures the analyte concentration in the fluid sample if the first measurement of the known concentration of the analyte in the first reference solution and the second measurement of the known concentration of the analyte in the first reference solution are sufficiently dissimilar and the second measurement of the known concentration of the first reference solution is sufficiently similar to the known concentration of the reference solution.

In another aspect of the invention, an electrochemical sensor system includes a first reference solution having a known concentration of at least one analyte. The system also includes an electrochemical sensor which analyzes the analyte to determine a first measurement and a second measurement of the known concentration of the analyte. The system also has a comparator to compare the known concentration, the first measurement of the known concentration, and the second measurement of the known concentration of the analyte. The system additional has a corrective action device which initiates corrective action if the first measurement of the analyte in the first reference solution is substantially similar to the second measurement of the analyte in the first reference solution and the first and second measurements are substantially dissimilar to the known concentration of the analyte. In one embodiment, a cartridge holds the first reference solution.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWING

The foregoing and other objects, features and advantages of the present invention disclosed herein, as well as the invention itself, will be more fully understood from the following description of preferred embodiments and claims, when read together with the accompanying drawings. The drawings are not necessarily to scale, emphasis instead generally being placed upon illustrating the principles of the invention.

FIG. 5 illustrates an embodiment of a corrective action report.

DETAILED DESCRIPTION OF THE INVENTION

Figure 1:
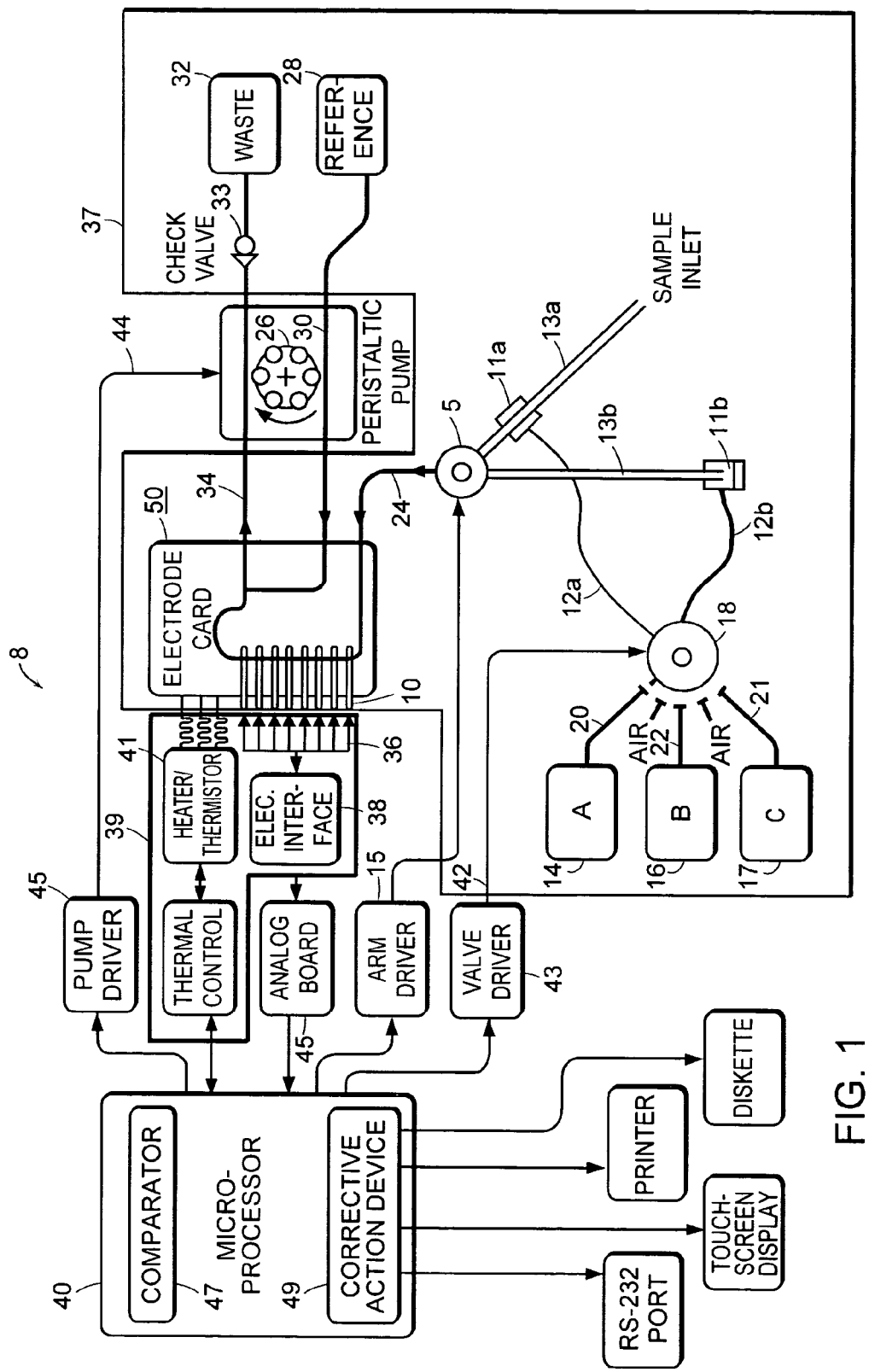
FIG. 1 is a schematic diagram of the components of an electrochemical sensor apparatus including a sensor cartridge with a bank of sensors and a thermal block for accelerated hydration and calibration of the sensors.

The present invention pertains to electrodes and electrochemical sensor systems for measuring analyte levels of aqueous samples including, but not limited to, blood serum or other body fluids. In one aspect, the invention is directed to reducing operator interaction for calibration of the system. The invention is further directed to a system for the continuous monitoring and continuous calibration of the sensors in the system. The present invention is also related to a method for determining failure patterns of and for recognizing the failure pattern and initiating remedial action to correct the error in the sensor indicated by the failure pattern.

Definitions

In order to more clearly and concisely point out and describe the subject matter which applicant regards as the invention, the following definitions are provided for certain terms used in the following description and claims.

As used herein, the term "electrode" refers to a component of an electrochemical device which makes the interface between the external electrical conductor and the internal ionic medium. The internal ionic medium, typically, is an aqueous solution with dissolved salts. The medium may also comprise proteins in a stabilizing matrix.

Electrodes are one of three types: working or indicator electrodes, reference electrodes, or counter electrodes. A working or indicator electrode measures a specific chemical species, such as an ion. When electrical potentials are measured by a working electrode, the method is termed potentiometry. All ion-selective electrodes operate by potentiometry. When current is measured by a working electrode, the method is termed amperometry. Oxygen measurement is carried out by amperometry. Working electrodes may also have an enzyme in an enzyme layer. The enzyme layer is part of a composite layer that is in close contact with the electrode. The enzyme, which is specific to a particular analyte, produces hydrogen peroxide, a by-product of the catalytic reaction of the enzyme on the analyte. Hydrogen peroxide is detected by the electrode and converted to an electrical signal. A reference electrode serves as an electrical reference point in an electrochemical device against which electrical potentials are measured and controlled. In one embodiment, silver-silver nitrate forms the reference electrodes. Other types of reference electrodes are mercury-mercurous chloride-potassium chloride or silver-silver chloride-potassium chloride. A counter electrode acts as a sink for the current path.

As used herein, the term "sensor" is a device that responds to variations in the concentration of a given chemical species, such as glucose or oxygen, in a sample, such as a body fluid sample. An electrochemical sensor is a sensor that operates based on an electrochemical principle and requires at least two electrodes. For ion-selective measurements, the two electrodes include an ion-selective electrode and a reference electrode. Amperometric enzyme electrodes additionally require a third electrode, a counter electrode. Moreover, enzyme sensors based on two electrodes (e.g., a working and reference electrode) are also common.

As used herein, the term "calibration" refers to the process by which the response characteristics of a sensor to a specific analyte are determined quantitatively. To calibrate a sensor, the sensor is exposed to at least two internal reference solutions, or process control solutions, each solution having a different, known concentration of the analyte. The responses, i.e., signals, measured by the sensor relative to the concentrations of the analyte in the two different internal reference solutions serve as reference points for measurements of the same analyte in samples having unknown concentrations of the analyte.

As used herein, the term "drift" refers to a measure of the difference between the value of a first reading by a sensor of a sample and a second reading by the same sensor analyzing the same sample.

As used herein, the term "verification procedures" refers to one or more techniques used to verify that one or more sensors are properly calibrated.

As used herein, the term "failure patterns" refers to any indicator given by the sensor to indicate that it is not calibrated correctly. For instance, a failure pattern may include a drift error in a certain direction.

One-point and two-point drift calculations for pH, pCO$_2$, Na, K and Ca may be calculated by the following algorithms described below.

Measured values for Na, K and Ca for two-point cal:

$$[Cm]_A = [C]_B * 10^{(A-B)/S'} \quad \text{mmol/L} \quad (1)$$

$$[Cm]_B = [C]_B * 10^{(B-B')/S'} \quad \text{mmol/L} \quad (2)$$

Measured values for Na, K and Ca for one-point cal:

$$[Cm]_B = [C]_B * 10^{(B_2-B')/S} \quad \text{mmol/L} \quad (3)$$

Measured values for pCO$_2$ for two-point cal:

$$pCO_2MA = pCO_2B * 10^{(B-A)/S'} \quad \text{mmHg} \quad (4)$$

$$pCO_2MB = pCO_2B * 10^{(B'-B)/S'} \quad \text{mmHg} \quad (5)$$

Measured values for PCO2 for one-point cal:

$$pCO_2MB = pCO_2B * 10^{(B'-B_2)/S} \quad \text{mmHg} \quad (6)$$

Measured values for pH for two-point cal:

$$pHMA = (B-A)/S' + pHB \text{ pH unit} \quad (7)$$

$$pHMB = (B'-B)/S' + pHB \text{ pH unit} \quad (8)$$

Measured values for pH for one-point cal:

$$pHMB = (B'-B2)/S + pHB \text{ pH unit} \quad (9)$$

In the algorithms above, the $[Cm]_A$ and $[Cm]_B$, pCO$_2$MA and pCO$_2$MB, or pHMA and pHMB are the measured A and B values. A and B before A are the two-point calibration. B' is the one-point calibration before the B or B$_2$. B$_2$ is the latest one-point calibration. S is the slope from the latest two-point calibration, and S' is the slope from the previous two-point calibration. $[C]_B$, pCO$_2$B and pHB are the "B" bar-code values. The drift is the difference between the measured and the bar-code value. In the drift calculations for two-point calibration, the S' is used as long as it can be calculated. If S' cannot be calculated, the S (current slope) is used in place of the S'. If there is a sample or "A" calibration between the "B" and "B'" or between the "B$_2$" and "B'", then the following equations are used for the measured "B":

$$[Cm]_B = [C]_B * 10^{(B_2-B')/(K*S)} \quad \text{mmol/L} \quad (10)$$

$$pCO_2MB = pCO_2B * 10^{(B'-B2)/(K*S)} \quad \text{mmHg} \quad (11)$$

$$pHMB = (B'-B_2)/(K*S) + pHB \text{ pH unit} \quad (12)$$

If there is a "C" calibration or "rinse" between the "B" and "B'" or between the "B$_2$" and "B'", then the following equations are used for the measured "B":

$$[Cm]_B = [C]_B * 10^{(B_2-B')/(K*S)} \quad \text{mmol/L} \quad (13)$$

$$pCO_2MB = pCO_2B * 10^{(B'-B2)/(K*S)} \quad \text{mmHg} \quad (14)$$

$$pHMB = (B'-B_2)/(K*S) + pHB \text{ pH unit} \quad (15)$$

In the equations above, K is a constant value representing a sensitivity factor. In one embodiment, a lower K value represents a less sensitive sensor system 8 with respect to the measurement of an A concentration and an even less sensitive sensor system 8 with respect to the measurement of a C concentration. In one embodiment, the range of values for K is approximately 1–3, where 1 represents the most sensitive and 3 represents the least sensitive. In some embodiments, the K value for an A concentration is preferably 1.5 and within the range of 1–2. In additional embodiments, the K value for a C concentration is within the range of 2–4. Moreover, in some embodiments, the K value represents a baseline and substantially equals 1 for B concentrations. Although described above as preferable ranges and values, the value of K can take on any value to represent the sensitivity factor associated with a particular concentration.

If there is a one-point drift failure, or error, for pH, PCO2, Na, K or Ca, and if the repeated calibration fails for drift, then, before reporting the drift failure, another drift check may be performed. In this alternate drift check, the B' in equations 3, 6, or 9 is replaced with the B mV prior to the drift failure. If this alternate drift check passes, then the repeated calibration should pass and should be reported. If this alternate drift check fails, then the initial repeated calibration (the retried calibration that failed) should be reported. In one embodiment, this process only applies to the first retry after a B drift error.

One-point and two-point drift Calculations for pO$_2$.
Oxygen Drift:

$$pO_2MA = (pO_2B - pO2C)*(A-C)/(B_2-C) + pO_2C \text{ mmHg} \quad (1)$$

$$pO_2 \text{ drift } A = pO_2MA - pO_2MA' \text{ mmHg}$$

$$pO_2MB = (pO_2B - pO2C)*(B_2-C)/(B'-C) + pO_2C \text{ mmHg} \quad (2)$$

$$pO_2 \text{ drift } B = pO_2MB - pO_2B \text{ mmHg}$$

$$pO_2MC = (pO_2B - pO_2C)*(C-C')/(B_2-C') + pO_2C \text{ mmHg} \quad (3)$$

$$pO_2 \text{ drift } C = pO_2MC - pO_2C \text{ mmHg}$$

pO$_2$MA, pOMB and pO$_2$MC are the measured oxygen in the Cal A, Cal B and Cal C respectively. pO$_2$MA' is the measured oxygen value from the previous Cal A (the very first value will be determined in warm-up). pO$_2$B and pO$_2$C are the oxygen values in the B bag and C bag, respectively. A is the oxygen mV value from the current Cal A. C is the oxygen mV value from the most recent Cal C. C' is the oxygen mV value from the previous Cal C. B' is the oxygen mV value from the Cal B before the B2. B2 is the oxygen mV value from the current Cal B.

Several exceptions for the oxygen drift calculations exist. If there is a sample or "A" calibration between the "B2" and "B'", then equation 2 is modified to:

$$pO_2MB = (pO_2B - pO_2C)*((B_2-B')/(K*(B'-C))+1) + pO_2C \quad (4)$$

If there is a "C" calibration or "Rinse" between the "B$_2$" and "B'", then equation 2 is modified to:

$$pO_2MB=(pO_2B-pO_2C)*((B_2-B')/(K*(B'-C))+1)+pO_2C \quad (5)$$

If there is a "B" drift failure for pO$_2$ and if the repeated calibration fails, then, before reporting the drift failure, another drift check may be performed. In this alternate drift check, the B' in equations 2 is replaced with the B mV prior to the drift failure. If this alternate drift check passes, then the repeated calibration should pass and be reported. If this alternate drift check fails, then the initial repeated calibration (the retried calibration that failed) should be reported. This process applies only to the first retry after a B drift failure.

Electrochemical Sensor System

Referring to FIG. 1, the electrochemical sensor system 8 employs a sensor assembly, generally indicated at 10, incorporating a plurality of electrodes adapted to make electrical measurements on a sample, such as a blood sample, introduced to the sensor assembly 10. Blood samples to be analyzed by the system 8 are introduced through a sample inlet 13a. Blood samples are obtained by, for example, phlebotomy or are derived on a periodic basis from an extracorporeal blood flow circuit connected to a patient during, for example, open heart surgery. Blood samples may be introduced into the sample inlet 13a through other automatic means, or manually, such as by syringe. The blood samples may be introduced as discrete samples.

The electrochemical system 8 can also contain a disposable cartridge 37. A cartridge of a similar type is set forth in detail in U.S. Pat. No. 4,734,184, U.S. Ser. No. 09/871,885, U.S. Ser. No. 09/872,240, and U.S. Ser. No. 09/872,247 the entirety of the specifications incorporated by reference herein. In one embodiment of the invention, the cartridge 37 also includes a rotor-for-sample inlet arm 5.

Referring to FIG. 1, in one embodiment of the invention, the electrochemical sensor system 8 incorporates in the cartridge 37 at least three prepackaged containers 14, 16, and 17, each containing an internal reference solution having known values of the parameters to be measured by the system 8. For purposes of reference, the solution contained within the prepackaged container 14 will be termed internal reference solution A, the solution contained within the prepackaged container 16 will be termed internal reference solution B, and the solution contained within the prepackaged container 17 will be termed internal reference solution C. Any prepackaged container 14, 16, and 17 however, can contain any internal reference solution (e.g., internal reference solution C). Each of the prepackaged containers 14, 16 and 17 contain a sufficient quantity of its internal reference solution to allow the system 8 to be calibrated a substantial number of times before the prepackaged container 14, 16, 17 becomes empty. In one embodiment, the system 8 is calibrated 1500 times for 'B', 150 times for 'A', and 20 times for 'C'. When one or more of the containers 14, 16 and 17 containing the internal reference solutions are empty, the cartridge containing prepackaged containers 14, 16 and 17 is replaced.

With continued reference to FIG. 1, in one embodiment, the prepackaged container 14 is connected to the input of a multi-position valve 18 through a flow line 20, and the prepackaged container 16 is connected to a second input of the multi-position valve 18 through a flow line 22. In yet another embodiment, the container 17 is connected to a third input of the multi-position valve 18 through a flow line 21. The output line 12 is the output of the multi-position valve 18 and is connected to the sample input line 13 through a stylus 11. Depending upon the position of the valve 18, the input lines 20, 21, 22 or air, is open to the valve 18. Similarly, when the stylus is in a normal position (position 11b) of the sample input line 13b, line 12b is open to the sample input line 13b and allows passage of the internal reference solution, or rinse solution, or air through the sample input line 13b to the sensor assembly 10 through line 24, facilitated by the operation of a peristaltic pump schematically illustrated at 26. In a sample accepting mode (13a) in which the input line is in position 13a, however, a line 12a is separated from the sample input line (position 13b) and the sample is introduced directly to the sensor assembly 10 through line 24, facilitated by the operation of the peristaltic pump 26.

Referring to FIG. 1, the cartridge 37 also includes a container 28 for a solution surrounding a reference electrode. The container 28 is connected to the sensor assembly 10 by a flow line 30. The system further includes a waste container 32, which receives the blood samples, the internal reference solution and the solution for the reference electrode 28 after they have passed through the sensor assembly 10. In one embodiment, the sensor assembly 10 transmits these samples (e.g., blood samples) to the waste container 32 via a flexible conduit 34.

Both the waste flow conduit 34 and the flow line 30 for the solution for the reference electrode includes sections of flexible walled tubing that pass through the peristaltic pump 26. The pump 26 compresses and strokes the flexible sections of the flow lines 30 and 34 to induce a pressured flow of solution for the reference electrode from its container 28 to the electrode assembly 10. This compression and stroking also creates a negative pressure on the waste products in flow line 34 so as to draw fluids in the flow line 24 through passages in the electrode assembly 10 past the membranes of the sensors. This arrangement, as opposed to the alternative of inducing positive pressure on the blood and calibrating solutions to force them through the electrode assembly 10, avoids the imposition of unnecessary and possibly traumatic mechanical forces on the blood sample, thereby minimizing the possibility of a leak in the electrode assembly 10.

Figure 2:
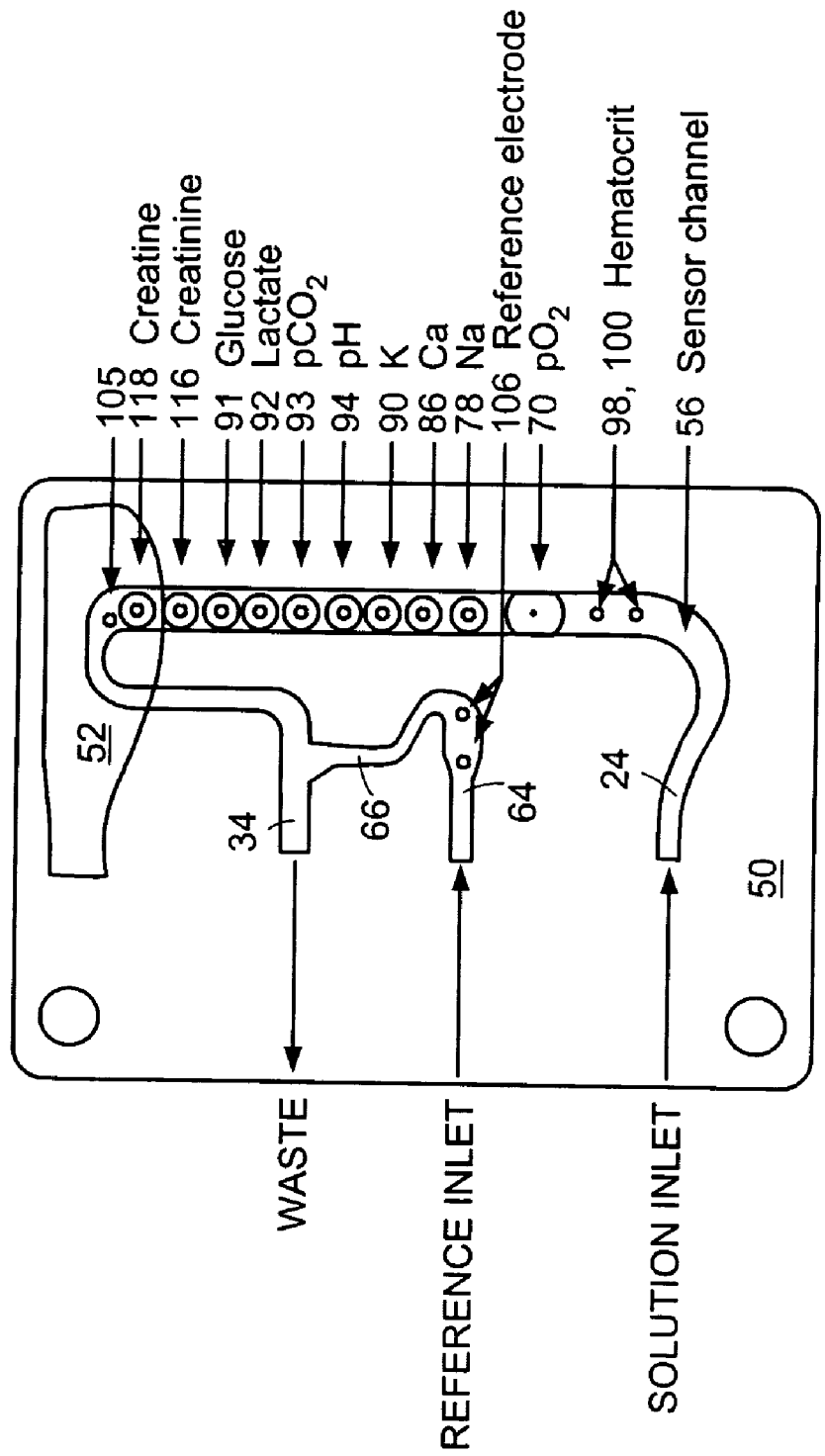
FIG. 2 illustrates a reverse frontal view of the sensor card, partly fragmentary, of a cartridge embodiment of the invention.

Cartridge 37 also contains a sensor card 50, illustrated for example in FIG. 2, which provides a low volume, gas tight chamber in which the sample, such as a blood sample, internal reference solution, or a monomer-containing solution, is presented to one or more electrochemical sensors, i.e., the pH, pCO$_2$, pO$_2$, Na$^+$, Ca$^{++}$, glucose, lactate, creatine, creatinine and hematocrit sensors. The sample and the reference electrode solution (from container 28) are integral parts of the chamber and are collectively indicated as the electrode assembly 10. Chemically sensitive, hydrophobic membranes typically formed from polymers, such as polyvinyl chloride, specific ionophores, and a suitable plasticizer, can be permanently bonded to the chamber body. These chemically sensitive, hydrophobic membranes are the interface between the sample or calibrating solutions and the buffer solution in contact with the inner (silver/silver chloride) electrode.

Blood samples that have been analyzed are prevented from flowing back into the sensor card 50 from the waste container 32 due to the presence of a one-way check 33 valve 33 in the waste line 34. After use in the system 8, the cartridge 37 is intended to be discarded and replaced by another cartridge.

Sensors may be available as a bank of electrodes 10 fabricated in a plastic card 50 and housed in the disposable cartridge 37 that interfaces with a thermal block assembly 39 of a suitably adapted blood-chemistry analysis machine. The thermal block assembly 39 houses the heating/cooling devices such as a resistive element or a Peltier-effect device, a thermistor 41 to monitor and control the temperature, the electrical interface 38 between the sensors in the plastic card 50 and a microprocessor 40 through an analog board 45. The analog board 45 houses analog-to-digital and digital-to-analog converters. The analog-to-digital converter receives the signal from the electrode interface 38 and converts it into a digital form for the processor 40 to store and display. The digital-to-analog converter also receives the digital signals from the processor 40 (e.g., the polarization voltage for oxygen sensor) and converts them into an analog form and subsequently transmits them to the sensors for control.

Referring still to FIG. 1, the electrochemical sensor system 8 is formed upon insertion of the cartridge 37 into the electrochemical sensor apparatus. Upon insertion, the sensor assembly 10 fits into the heater block assembly 39, described in detail below, and the heating/cooling assembly regulated by the microprocessor 40 cycles the temperature of the sensor electrode card 50 and the solution in contact with the sensors inside the electrode card 50 through a specific temperature for a specified duration. The heater block assembly 39 is capable of rapid heating and cooling by, for example, a thermoelectric device applying the Peltier-effect. In one embodiment, the heater block assembly 39 is monitored by thermistor 41 and both are controlled by the microprocessor 40.

The electrode assembly 10 may also have a number of edge connectors 36 in a bank which allow it to be plugged into a female matching connector of the electrical interface 38 so that the electrodes formed on the assembly 10 may be connected to microprocessor 40 through the analog board 45. The microprocessor 40 is connected to the multiport valve 18 via a valve driver 43 by a line 42 and to the motor of the peristaltic pump 26 via a pump driver 45 by a line 44. The microprocessor 40 controls the position of the sample arm 5 through arm driver 15. The microprocessor 40 also controls the position of the valve 18 and the energization of the pump 26 to cause sequences of blood samples, internal reference solutions, and external verification solutions to be passed through the electrode assembly 10. When the internal reference solutions from, for example, containers 14, 16 and 17 are pumped into the electrode assembly 10, the electrodes forming part of the assembly make measurements of the parameters of the sample and the microprocessor 40 stores these values. Based upon measurements made during the passage of the internal reference solutions through the electrode assembly 10, and the known values of the measured parameters contained within the internal reference solutions from containers 14, 16, and 17, the microprocessor 40 effectively creates a calibration curve for each of the measured parameters. Thus, when a blood sample is passed through the electrode assembly 10, the measurements made by the electrodes can be used to derive accurate measurements of the parameters of interest. These parameters are stored and displayed by the microprocessor 40. The microprocessor 40 is suitably programmed to perform measurement, calculation, storage, and control functions such as differences in electrical potential across one or more electrodes.

Illustrated in FIG. 1, in one embodiment, the microprocessor 40 also includes a comparator 47 to compare the measurements of concentration of the analyte being analyzed, as described in more detail below. As shown, the comparator may be part of the microprocessor 40. The comparator can be, for example, any digital or analog circuit, such as an AND gate.

Figure 4A:
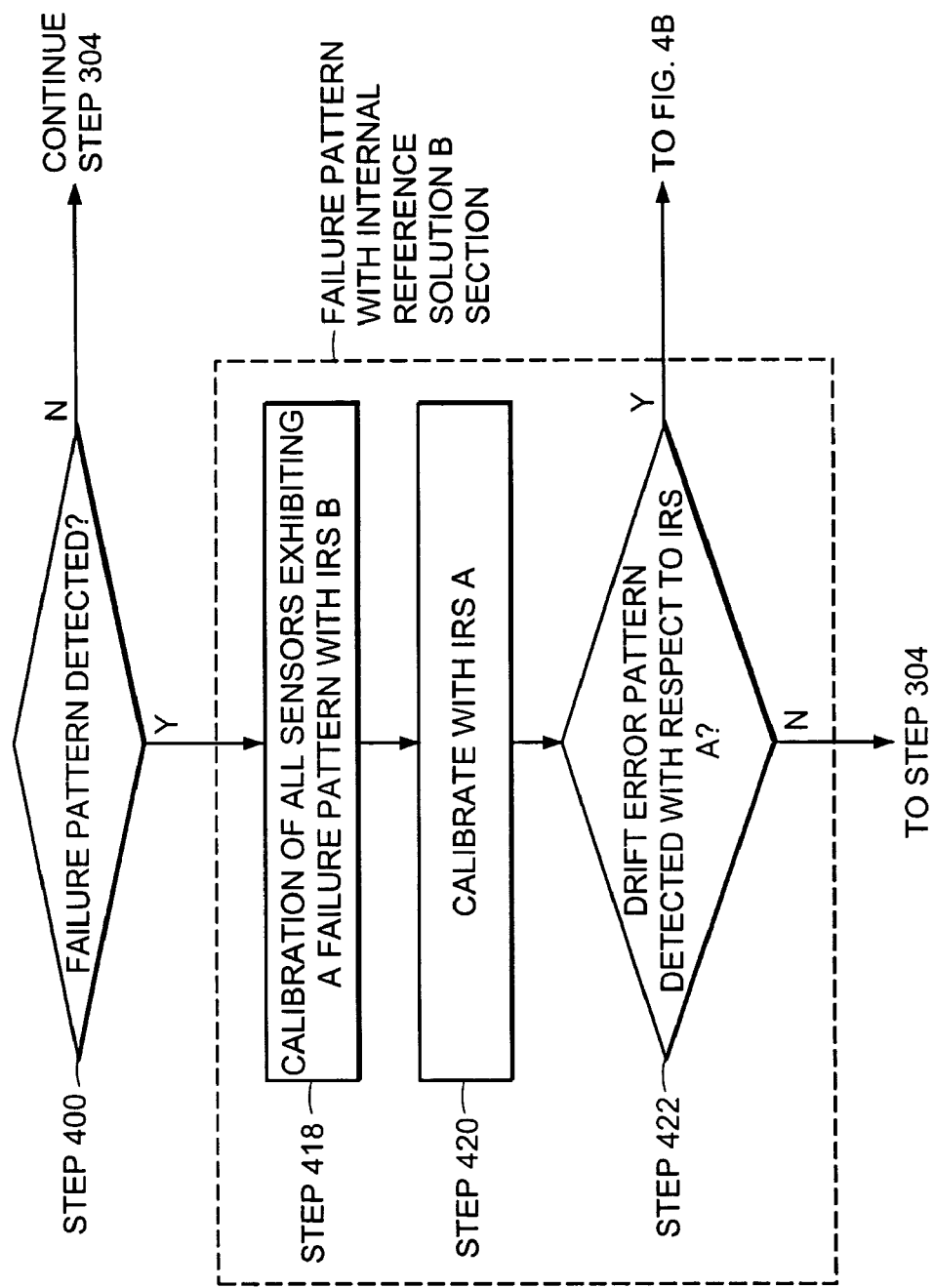
FIGS. 4A–4B illustrate failure patterns and corrective actions related to internal reference solution B.
Figure 4B:
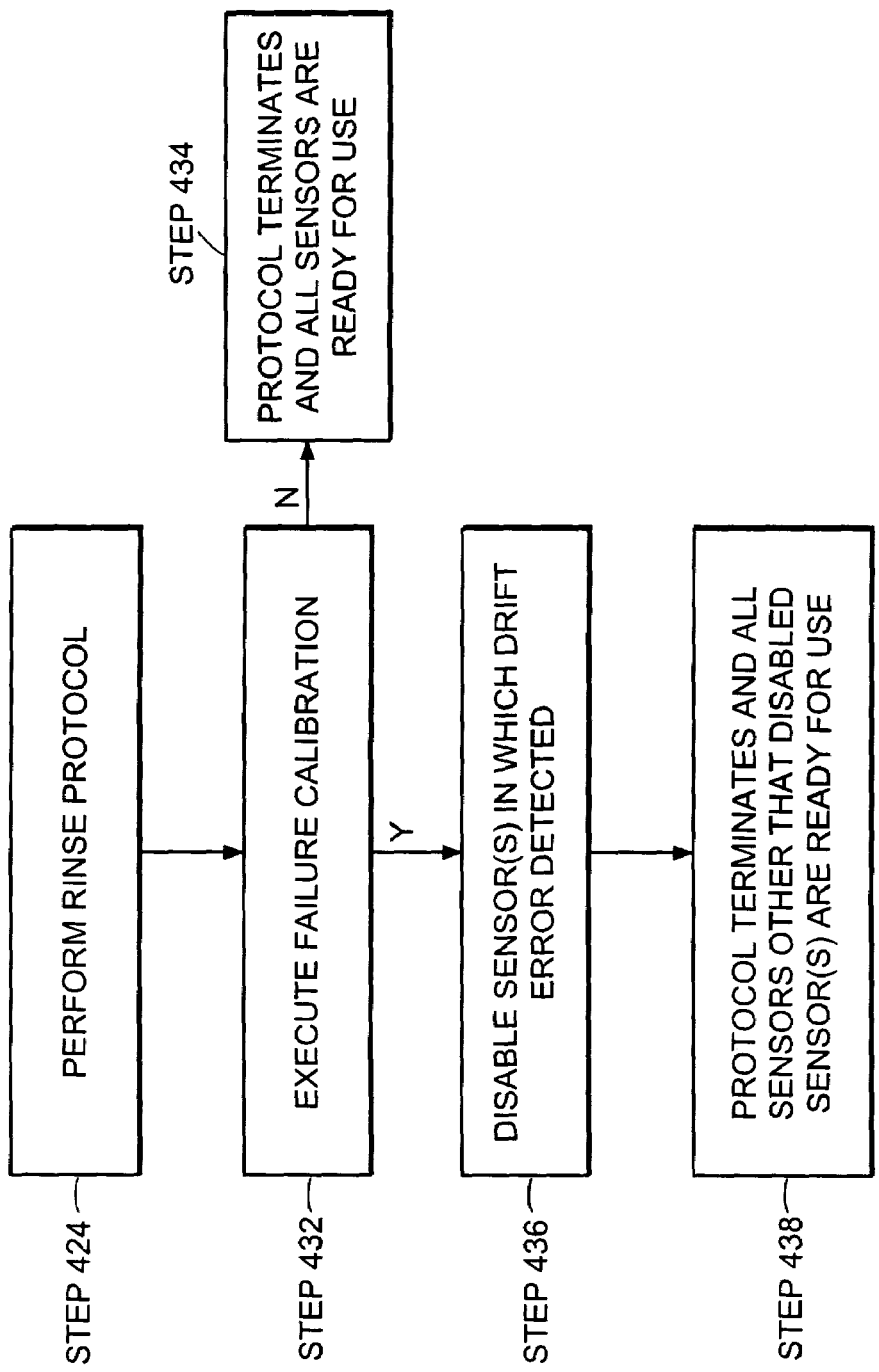

Additionally, the corrective action performed by the electrochemical sensor system 8, as described in more detail below with respect to FIGS. 4A–4B, are performed by a corrective action device. The corrective action device may be a component of the microprocessor 40. The corrective action device may also be a module or software program executed by the microprocessor 40. Although shown as an internal component of the microprocessor 40, the corrective action device 49 and/or the comparator 47 can alternatively be devices externally located from the microprocessor 40.

Internal Reference Solutions

In one embodiment of the invention, a composition of internal reference solution A used for second point calibration is prepared at, for example, 37° C. and at atmospheric pressure tonometered with 9% $CO_2$, 14% $O_2$, and 77% Helium gas, and has the following characteristics: pH 6.9 organic buffer; $pCO_2$=63 mmHg; $pO_2$=100 mmHg; $Na^+$=100 mmol/L; $K^+$=7 mmol/L; $Ca^{++}$=2.5 mmol/L; glucose=150 mg/dL; lactate=4 mmol/L; creatine=0.5 mmol/L; creatinine=0.5 mmol/L; surfactant and inert preservative.

In further embodiments of the invention, a composition of internal reference solution B used for one-point calibration and rinse is prepared at, for example, 37° C. and at 700 mmHg absolute pressure tonometered with 27% $O_2$, 5% $CO_2$, and 68% Helium gas, and has the following characteristics: pH 7.40 organic buffer; $pCO_2$=34 mmHg; $pO_2$=180 mmHg; $Na^+$=140 mmol/L; $K^+$=3.5 mmol/L; $Ca^{++}$=1.0 mmol/L; 20 mM choline chloride; surfactant and inert preservative.

In yet other embodiments of the invention, a composition of internal reference solution C used for third-point calibration (for $pCO_2$ and pH), cleaning, low level oxygen calibration and in situ regeneration of the inner polymeric membrane for the enzyme sensors has the following characteristics: NaOH=12 mM, $NaHCO_3$=86 mM, $Na_2SO_3$=20 mM, total $Na^+$=140 mM; KCL=6 mM; 15 mmol/L of m-phenylenediamine; 50 mM 3-[(1,1-Dimethyl-2-hydroxyethyl)amino]-2-hydroxypropanesulfonic acid (AMPSO); 4.5 g/L polyoxyethylene (100) stearyl ether (Brij 700); 4.5 g/L Polyoxyethylene (35) castor oil (Cremophor EL); 3 g/L Polyoxyethylene fatty glyceride (Arlatone G); and 3 g/L block copolymer of ethylene oxide and propylene oxide (Tetronic 90 R4). Additionally, the solution for the reference electrode (stored in container 28) may contain $AgNO_3$=1 mmol/L; $KNO_3$=1 mol/L; and surfactant.

The compositions of the internal reference solutions A and B are chosen so that, for each of the characteristics measured by the system, a pair of values are obtained that are spaced over the range of permissible values, thereby providing a balanced 2-point calibration for the instrument. The internal reference solution C is chosen for low level oxygen calibration and regeneration of the inner polymeric membrane in the glucose, creatine, creatinine and lactate sensors.

In one embodiment, the A and B internal reference solution compositions are prepared by premixing all of the constituents in a certain order, such as by starting with the buffer and ending with the sodium bicarbonate salt, and then tonometering the solution with oxygen and $CO_2$ mixed with helium to produce the desired level of $pCO_2$ and $pO_2$.

In one embodiment, the C internal reference solution is prepared with a slightly different procedure. Specifically, the salts, with the exception of sodium sulfite, m-phenylenediamine and sodium bicarbonate, are added to water and the solution is tonometered with helium to bring the $pO_2$ to less than 30 mmHg. The remaining salts are then added to the solution, and the final mixture is tonometered with mixture of $pCO_2$ and helium to produce the desired $pCO_2$ level.

In one embodiment, at least one electropolymerizable monomer is added to at least one of the internal reference solutions, C in container 17, for example. The absence of dissolved oxygen in the C internal reference solution, due to the presence of sulfite ion, allows for a longer shelf life of electropolymerizable monomer in C because dissolved oxygen will oxidize the electropolymerizable monomer and thus render the monomer incapable of polymerizing. The electropolymerizable monomers (e.g., m-phenylenediamine) may be included in an internal reference solution at a concentration in a range between about 1 to 100 mM, preferably 15 mM. The electropolymerizable monomer may also be included in the cartridge 37 in a separate reservoir.

The temperature and pressure at which the internal reference solutions are prepared and their method of packaging are such as to preclude the possibility of dissolved gases going out of the solution in the container 14, 16, 17. This can affect the concentration of gases in the calibrating solutions and/or minimize the tendency for gases to permeate through materials.

The internal reference solutions are packaged with the solutions completely filling the containers, so that there is no headspace, by evacuating the containers prior to filling. By filling the internal reference solution into the evacuated flexible wall container 14, 16, 17 at elevated temperatures and subatmospheric pressure, the solution will not have any tendency at a lower use temperature to outgas and thus produce gas bubbles in the container. Were outgassing to occur, the concentrations of the gases in the solution would be affected, creating an inaccuracy in the calibration of the instruments. Similarly, the internal reference solutions are not packaged at too low of a pressure (e.g., not below about 625 mm of mercury) because the absorptive capacity of the solution for gases conceivably increases as the packaging pressure decreases. Moreover, below that pressure value, the absorptive capacity of the solution may be sufficiently high so that the pressure value will tend to draw gases in through the slightly inherent permeability of even the most gas-impervious flexible packaging material over long periods of time. Accordingly, a packaging pressure in the range of 625–700 mm of mercury is preferred.

In one embodiment, an internal reference solution is prepared at a temperature in excess of its intended-use temperature so that, at the lower temperature, there is less tendency for outgassing of the dissolved gases. This solution may work in conjunction with the reduced pressure packaging to minimize the possibility of outgassing.

In one embodiment, internal reference solutions A and B are prepared at a temperature above their intended-use temperature at a controlled pressure close to atmospheric pressure. Through the use of an elevated temperature (e.g., 37° C.) the solution may be prepared at about atmospheric pressure without any possibility of subsequent microbubbles within the container or gas transfer through the container. This may occur, for instance, when the solutions are packaged in a zero head-space, flexible gas-impervious container.

The envelopes used to create the prepackaged containers 14, 16, 17 are formed, for example, with rectangular sheets, heatsealed at the edges and heatsealed at one corner to an inlet stem of the valve 18. The inlet stem of the valve 18 can be used, for example, for filling purposes. In one embodiment, the prepackaged containers 14, 16, and 17 and the prepackaged container lines 20, 22, and 21 are formed in a unitary cluster with the valve 18 so that gas-phase dead space in the lines 20, 22, 21 is avoided. In a preferred embodiment for purging and filling the envelope bags, the envelope is evacuated and then filled with the prepared solution. The bag is then shaken while the excess solution flows out of the bag. This process removes any residual gas bubbles from the bag. The solution is then sealed in the container.

Solution for the Reference Electrode

The solution for the reference electrode disposed in prepackaged container 28 is employed in the electrode assembly 10 as a supply source to a reference electrode. The reference electrode solution can provide a liquid junction and thereby isolate the reference electrode from the varying electrochemical potential of the internal reference solution or the blood in a manner which will be subsequently described. In a preferred embodiment, the solution is 1 mol/L potassium nitrate and 1 mmol/L silver nitrate solution. The solution may also contain a surfactant such as Brij 35. The solution is packaged in a sealed flexible container with no headspace. The solution for the reference electrode is not an internal reference solution and does not function similarly to the internal reference solutions A, B, and C.

Electrode Assembly

During operation of the pump 26, the electrode assembly 10 can receive a constant, pulsating flow of the solution for the reference electrode via line 30 and sequential, intermittent, pulsating flows of either the blood sample or one of the internal reference solutions via line 24. The assembly may also provide a corresponding output of its waste products to the waste collection bag 32.

Referring also to FIG. 2, by way of example, the electrode assembly 10 in a preferred embodiment consists of a structurally rigid rectangular card 50 of polyvinylchloride having a rectangular aluminum (or other suitable material) cover plate 52 adhered to one of its surfaces. The cover plate 52 closes off the flow channels 56 formed in one surface of the card 50. The cover plate 52 can also act as a heat transfer medium for hydrating the sensors by thermal cycling, described below. Moreover, the cover plate 52 can maintain the fluids flowing through the electrode assembly 10, and the electrodes themselves, at a constant temperature during calibration and during measurement of relevant parameters in a patient sample. This may be achieved by measuring the temperature of the plate 52 and employing a suitable heating or cooling element, e.g., a Peltier-effect device and thermistor 41, to maintain the temperature of the plate 52 at a desired temperature.

A solution for the reference electrode is introduced to a well 64, formed in the surface of the substrate 50 in the same manner as the other flow channels 56 and similarly covered by the metal plate 52. The solution for the reference electrode flow line 30 passes through an inclined hole in the well 64. The well 64 is connected to the output section 34 of the flow channel 56 through a very thin capillary section 66 formed in the surface of the plastic substrate 50 in the same manner as the main flow channels 56. The capillary channel 66 can be substantially shallower and narrower than the main flow channel 56. In one embodiment, the cross section of the capillary channel 66 is approximately 0.5 sq. mm.

The pump 26 pumps solution for the reference electrode into the well 64 via line 30 (see also FIG. 1). The solution fills the well, and is then forced through the capillary section 66. The solution subsequently joins the output stream of fluid passing through the main flow channel section 56 and then flows with it to the waste bag 32. The combined influence of its higher density and the capillarity of the flow channel 66 serves to minimize any possibility of internal reference solution or blood passing downward through the channel 66 to the well 64 and affecting the electrochemical measurements.

As a blood sample or internal reference solution quantity introduced into the flow channel 24 passes through the flow channel 56 to the output section 34, it passes over a number of electrodes as illustrated in FIG. 2. For example, the blood sample and/or internal reference solution can be passed over a $pO_2$ sensor 70, an $Na^+$ sensor 78, a $Ca^{++}$ sensor 86, a $K^+$ sensor 90, a glucose sensor 91, a lactate sensor 92, a $pCO_2$ sensor 93, a pH sensor 94, hematocrit sensors 98, 100, a creatinine sensor 116, and a creatine sensor 118.

Also referring to FIG. 1, the heat plate 52 abuts and forms one wall of the sample channel 56. The heat plate 52 is in contact with the Peltier-effect device of the thermal block assembly 39 described below. The thermal block assembly 39 is capable of changing and controlling the temperature of the heat plate 52 between 15° C. and 75° C. The temperature change and control is monitored by a thermistor 41 and regulated by the microprocessor 40. An internal digital clock of the microprocessor 40 may control time and may further cause the microprocessor to apply power to the thermal block assembly 39 according to a preset program. Thus, the microprocessor 40 controls the thermal block assembly 39, regulating the temperature setting and the duration of each set temperature of the heat plate 52.

Support

Referring again to FIG. 1, the electrodes of the present invention are supported by the electrode, or support, card 50. The electrode card 50 may be comprised of any material capable of bearing, either directly or by virtue of some intervening adhesion-improving layer, the other necessary portions of the electrode which are described in detail hereinafter. Thus, the support may comprise materials such as ceramic, wood, glass, metal, paper or cast, extruded or molded plastic and/or polymeric materials, etc. In one embodiment, the composition of the support carrying the overlying electrode components is inert. Thus, it does not interfere with the potentials observed, for example, by a reaction with one of the overlying materials in an uncontrolled fashion. Moreover, the composition of the support withstands elevated temperatures to which the sensors can be exposed, such as during the time required to hydrate and/or calibrate the sensors. In the case of porous materials such as wood, paper or ceramics, the pores of the material may be sealed before applying the overlying electrode components. The means of providing such a sealing are well known in the art.

According to a preferred embodiment of the present invention, the support comprises a sheet or film of an insulating polymeric material. A variety of film-forming polymeric materials are well suited for this purpose, such as, for example, cellulose acetate, poly(ethylene terephthalate), polycarbonates, polystyrene, polyvinylchloride, etc. The polymeric support may be of any suitable thickness, typically from about 20–200 mils. Similarly, thin layers or surfaces of other materials mentioned above could be used. Methods for the formation of such layers are well known in the art.

Initial Operation of the Electrochemical Sensor System

When the cartridge with the sensor assembly 10 and the filled internal reference solution bags 14, 16 and 17 are first used, the valve 18 is controlled to direct one of the internal reference solutions, for example internal reference solution B, into the sensor assembly so it entirely fills the flow channel. The pump is then stopped for a predetermined period of time (e.g., 10–30 minutes, preferably 12–15 minutes) during which the dry chemical sensor electrodes are hydrated by thermal cycling (e.g., from 37° C. to 60° C. and back to 37° C.).

In one embodiment of the invention, the dry chemical electrode sensor assembly 10 is inserted into the electrochemical sensor system 8 and the valve 18 is controlled by the microprocessor 40 to direct the internal reference solution B into the sensor assembly 10. Thermal block assembly 39 is set at a temperature whereby the temperature of thermal plate 52 is sufficient to heat the calibrating solution in contact with the dry chemical sensor to a predetermined temperature (e.g., temperature in a range of 55° C. to 75° C., preferably 60° C.), for a predetermined time (e.g., 10–30 minutes, preferably 12 minutes). After the specified time period, the microprocessor 40 reverses current flow through the thermoelectric device to cool thermal plate 52. The sensor card 50 and internal reference solution in contact with thermal plate 52 are cooled to a cooling temperature (e.g., 37° C.). The temperature, controlled by the microprocessor 40, is maintained at the cooling temperature (e.g., 37° C.) for the life of the cartridge 37.

After hydration of the sensors, the conditioning cycle of the enzyme electrodes starts by pumping the C internal reference solution 17 to the sensor card 50 and soaking the electrodes for a predetermined soaking time (e.g., 1 to 6 minutes, preferably for 3 minutes) while the polarization potential of the enzyme electrodes is elevated from a normal voltage (e.g., 0.25 V) to an elevated voltage (e.g., 0.5 V) relative to the reference electrode. During the exposure to the C internal reference solution 17, the low oxygen level is calibrated. Upon completion of the C cycle, the rinse cycle starts by pumping rinse solution from prepackaged container 17 to the flow channel 56 by the peristalic pump 26. During the rinse cycle, the polarization potential of the enzyme electrodes is changed from 0.5 to 0.4 V in order to accelerate the removal of the residues of the internal reference solution C (from an inner interference rejection membrane). Following the completion of the rinse cycle, the polarization potential of the enzyme electrodes is lowered back to its normal level (e.g., about 0.25 V) relative to the reference electrode.

The sensors are then calibrated with respect to internal reference solutions A 14 and B 16. The cartridge 37 typically becomes ready for sample measurement within 30 minutes of cartridge 37 insertion into the electrochemical sensor system 8.

Operation of the Assembly

Following the initial operation of the electrochemical sensor system 8 and before the sensor system 8 is ready for use, the calibration of the sensors is verified. The verification step occurs once in the life of the sensor cartridge and uses external verification solutions to test the calibration of the sensors. The verification procedure begins when external verification solutions, including known concentrations of at least one analyte, are introduced into the sensor channel and analyzed by the sensors in the cartridge. Two different external verification solutions having different concentrations of the analyte are analyzed to obtain two different analyte concentration points for each sensor.

Figure 3A:
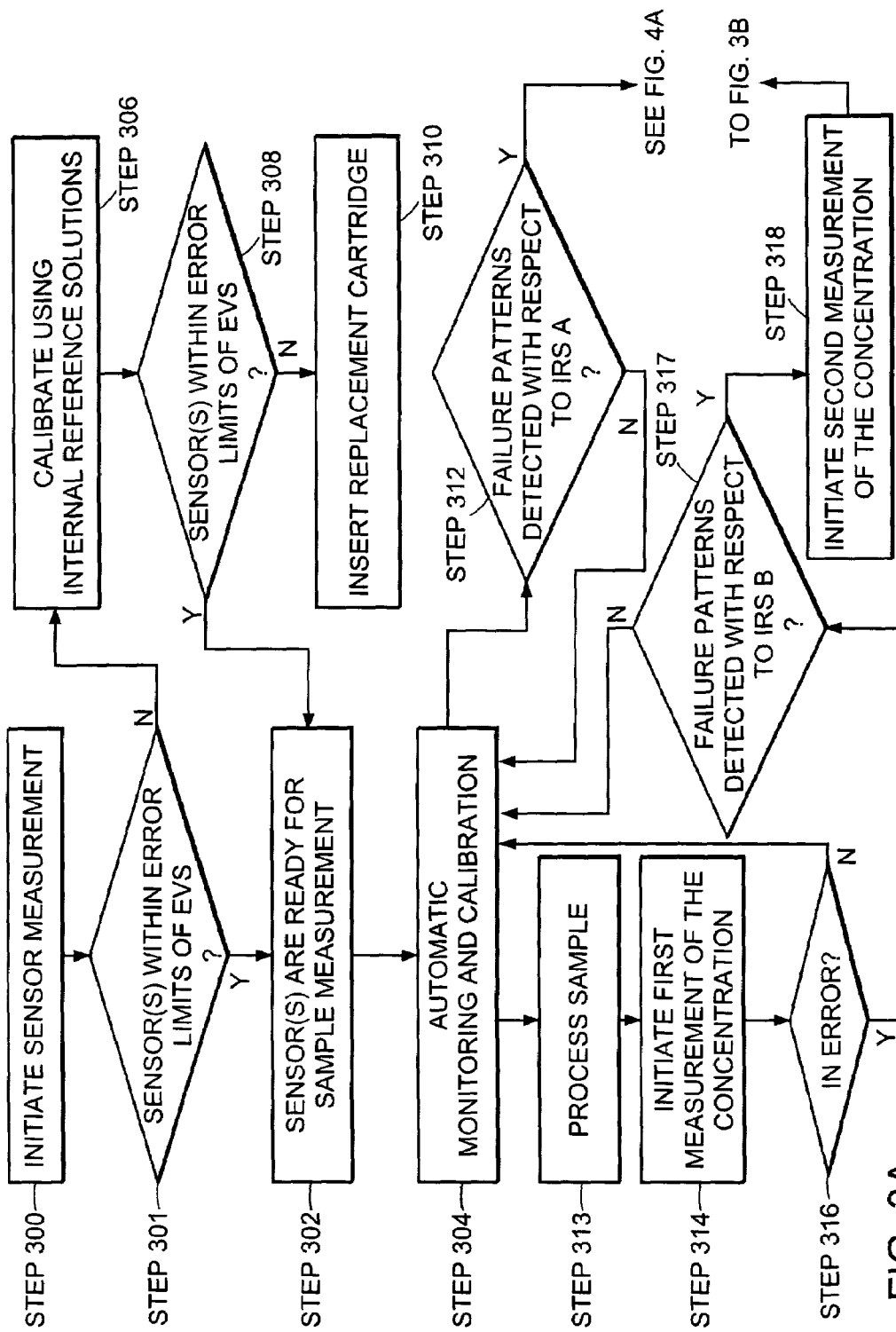
FIGS. 3A–3C illustrate a method of the electrochemical sensor system operation.

Referring to FIG. 3A, the electrochemical sensor system 8 initiates a sensor measurement (STEP 300) of the concentration of the external verification solutions (EVS). It is then determined if the sensor measurements are within the pre-set error limits with respect to the external verification solutions (STEP 301). The sensors are ready for sample measurement (STEP 302) if the concentration of the analyte in both external verification solutions fall within an acceptable range of a predetermined concentration of the analyte. An example of an acceptable range is within 5% of the known analyte concentration. If the sensors are ready for sample measurement (STEP 302), then the electrochemical sensor system begins the automatic monitoring and calibration of the sensors (STEP 304). During the automatic monitoring and calibration of the cartridge 37, the system automatically monitors the calibration of the sensors in the cartridge 37 using the internal reference solutions and initiates calibration of any sensor that measures an analyte concentration outside of a preset acceptable concentration range.

Following the initial verification of the calibration of the cartridge 37 by external verification solutions (STEP 301), the cartridge typically does not need any further hands-on monitoring by the operator during the useful life of the cartridge, even if re-calibration is required. However, if, during the initial verification (STEP 301), the concentration of the analyte measured by one or more sensors is determined to be outside of the predetermined acceptable range for the measured analyte concentration, calibration of the cartridge 37 using one ore more of the internal reference solutions is automatically initiated (STEP 306). After the calibration of the sensors (STEP 306), the initial verification procedure performed in STEP 301 is repeated (STEP 308). The sensors are ready for sample measurement (STEP 302) if all sensors measure the concentration of an analyte to have a value within a predetermined acceptable range. If, during the repeated initial verification procedure (STEP 308), it is determined that the sensors are not properly calibrated, the cartridge 37 is removed and a replacement cartridge 37 is introduced into the system (STEP 310). Although described as being repeated twice, the determination of whether the sensors are properly calibrated may occur any number of times.

Further, the electrochemical sensor system 8 can record any or all information associated with one or more of the sensors, such as a calibration reading, at any time. In particular, the electrochemical sensor system 8 can record this information in a storage element, such as in memory (e.g., random access memory), a disk drive, a hard drive, or a database. Moreover, the electrochemical sensor system 8 may also flag particular stored information, such as if data is outside the acceptable range. This flag can designate data with an "error status" to indicate one or more values which are outside an acceptable range of values.

Automatic Monitoring and Calibration

Referring still to FIG. 3A, the electrochemical sensor system 8 of the present invention can include an automatic sensor maintenance system that continuously and automatically monitors and calibrates each sensor within the system (STEP 304). The monitoring and calibration of each sensor (STEP 304) occurs at regularly scheduled timed intervals during which at least one of the internal reference solutions A, B, and C is continuously analyzed by the sensor(s) to verify the accurate calibration of the sensor(s) in the system. The continuous monitoring of each sensor is interrupted only during a sample measurement due to the sample displacing the internal reference solution from the sensor channel 56 or during a cleaning or calibration protocol. The use of at least one of the internal reference solutions A, B, and C for monitoring the calibration of each sensor eliminates the need for a periodic external calibration monitoring procedure (quality control) which uses an external verification solution.

Replacing an external monitoring procedure with an automatic monitoring procedure using the internal reference solutions to check for calibration of the sensor(s) eliminates the need for frequent hands-on monitoring of the system by the operator using external verification solutions. The system of the present invention also uses the internal reference solutions A, B, and C on a continuous basis to calibrate each sensor in the system when the monitoring procedure determines that one or more sensor is uncalibrated. The calibration of the sensor occurs automatically according to the invention rather than manually. Following the calibration of each sensor, the system 8 automatically performs a verification procedure to determine if each sensor is properly calibrated. The verification procedure is performed using the internal reference solutions.

During STEP 304 of FIG. 3A, the sensor system 8 continuously monitors for failure patterns of one or more sensors. The sensor system 8 periodically (e.g., every four hours) checks for A calibration. If the sensor system 8 detects a failure pattern with respect to internal reference solution A in STEP 312, then the sensor undergoes further failure pattern analysis and corrective actions, described in more detail in FIG. 4A. If the sensor system 8 does not detect a failure pattern with respect to internal reference solution A in STEP 312, the automatic monitoring and calibration continues.

All sensors in the cartridge 37 are monitored continuously (STEP 304) with reference to the internal reference solution(s) within the cartridge. The sensor system 8 processes the sample (STEP 313). The continuous analysis of the system includes the first measurement of the concentration of at least one analyte in the internal reference solution immediately after processing sample (STEP 314). It is then determined whether the concentration of an analyte in the internal reference solution measured by the sensor is outside the limits of the predetermined acceptable range (i.e., in error) (STEP 316). If the determined concentration of the analyte in the internal reference solution is not outside the predetermined acceptable range, then the automatic monitoring and calibration continues (STEP 304) and the cartridge is ready for a sample. If, during the monitoring of the internal reference solution (STEP 304), a determination of the concentration of an analyte (first measurement) is detected by a sensor in a range outside a predetermined acceptable range (STEP 316), then the system determines whether a failure pattern is detected with respect to internal reference solution B (STEP 317). If a failure pattern is detected, the system 8 initiates another reading (second measurement) of the sensor with respect to the same internal reference solution (STEP 318). If a failure pattern is not detected, the system 8 continues with its automatic monitoring and calibration (STEP 304).

Figure 3B:
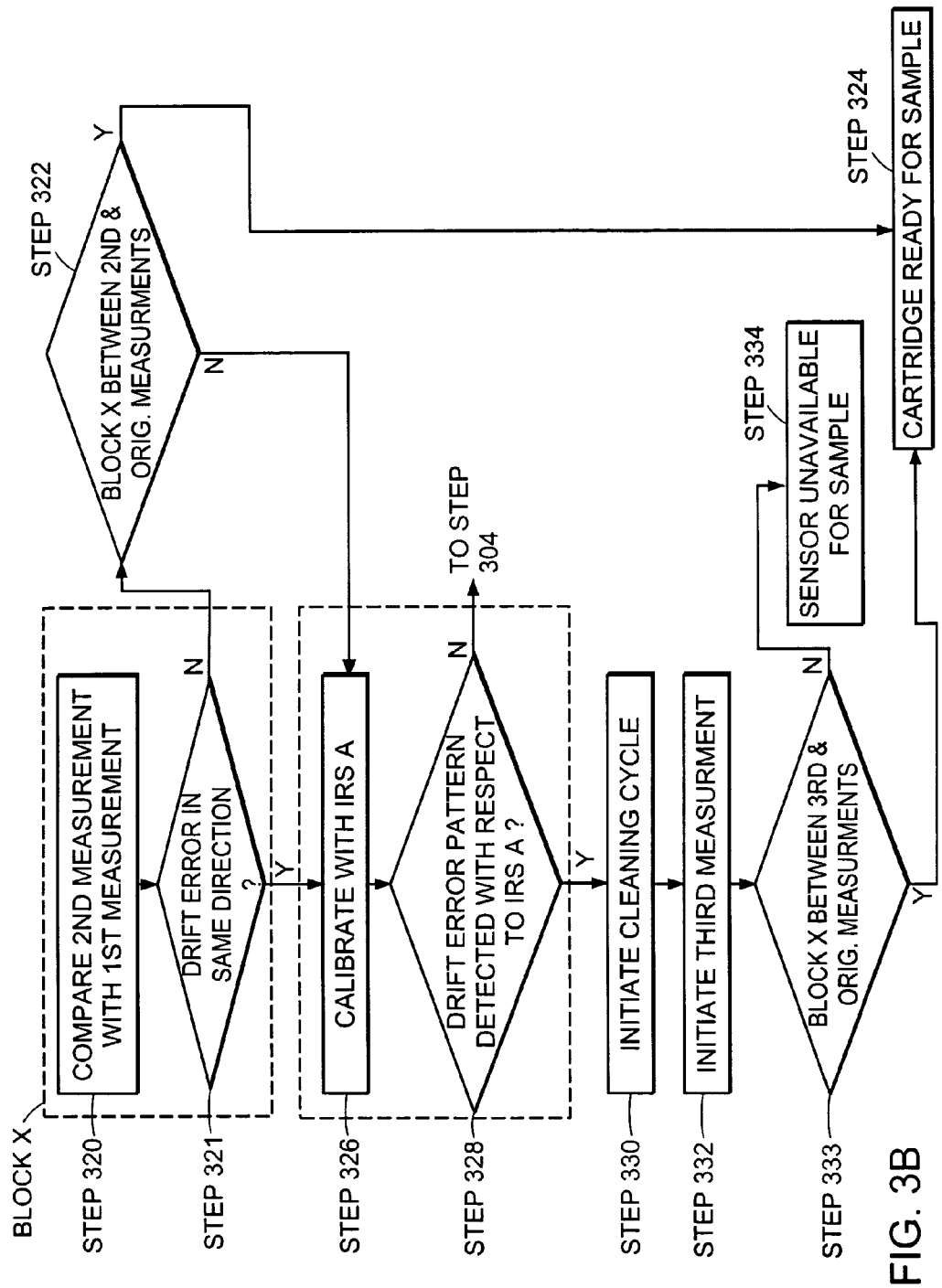

Also referring to FIG. 3B, the sensor system 8 then compares the concentration of the second measurement (from STEP 318) with the concentration of the first measurement (from STEP 314) (STEP 320). The system 8 then determines from this comparison if the drift error of the first measurement occurs in the same direction as the drift error of the second measurement (e.g., if both drift error values are positive or both drift error values are negative) (STEP 321). Further, STEP 320 and STEP 321 may together be referred to below as Block X.

If the drift error between the first measurement and the second measurement are not both errors in the same direction (i.e., one drift error is positive while the other drift error is negative) (STEP 321), then the sensor system 8 performs the operations in Block X with respect to the second measurement and the original measurement of the analyte in STEP 322. If the drift error of the second measurement is in the same direction as the drift error of the original measurement prior to the sample that caused the problem, then the system is ready to analyze a sample (STEP 324).

If, in STEP 321, the drift error of the second measurement is in the same direction (e.g., both positive or both negative) as the first measurement, the sensor system 8 then calibrates the sensor with internal reference solution A (STEP 326). The system 8 then determines if a drift error pattern has been detected with respect to internal reference solution A (STEP 328). If no drift error pattern has been detected, the system 8 returns to the automatic monitoring and calibration (STEP 304).

If, however, the system 8 detects a drift error pattern with respect to internal reference solution A (STEP 328), the system 8 initiates a cleaning cycle of the sensor (STEP 330). Following the cleaning cycle of the sensor (STEP 330), the sensor system 8 again analyzes the concentration (third measurement) of the analyte in the internal reference solution (STEP 332). The system 8 then executes the steps in Block X with respect to the third measurement and the original measurement prior to the sample that caused the problem (STEP 333). If both drift errors are in the same direction, then the cartridge 37 is ready for sample (STEP 324). If, however, the drift error of the third measurement is not in the same direction as the drift error of the original measurement (STEP 333), then the sensor is unavailable for sample (STEP 334).

With continued reference to FIG. 3B, if the drift error of the second measurement is not in the same direction as the drift error of the first measurement (STEP 321) and the drift error of the second measurement is the same direction as the drift error of the original measurement (STEP 322), the sensor is ready for a sample measurement (STEP 324). If, on the other hand, the drift error of the second measurement is determined not to have the same direction as the drift error of the original measurement (STEP 322), the sensor is again calibrated with internal reference solution A (STEP 326). Thus, in one embodiment, the comparison of drift error directions for different measurements occurs three times before stating that the cartridge 37 is unavailable to sample. In one embodiment, the comparisons between the measurements of the concentrations described above (and below) are performed by the comparator 47 illustrated in FIG. 1.

Sensor Failure Pattern Analysis and Recognition

The present invention includes a method for determining failure patterns of the electrochemical sensor system. Included in the present invention are systems and methods for detecting sensors which have become uncalibrated but have not been detected or corrected by the automatic monitoring and calibration system. Such sensors exhibit failure patterns that may be later used to identify these uncalibrated and undetected sensors.

The method of determining failure patterns includes the steps of examining the performance of cartridges 37 that include at least one uncalibrated sensor to identify characteristic failure patterns of the cartridge 37. The failed cartridges, which include at least one uncalibrated sensor, are selected by testing the calibration of the sensors with external verification solutions. Thus, the selected cartridges are cartridges which were determined by the above-described internal, automatic monitoring and calibration methods to be ready for sample measurement (STEP 324), but, as determined by an external verification procedure, the sensors in these cartridges were not calibrated properly. Determining the cause, failure pattern and corresponding corrective action of the failed cartridges allows for improvements to be made to the automatic monitoring and calibration method of the system to prevent undetected failure of the same type. The corrective action(s) are performed by the corrective action device 49.

Failure patterns and corresponding corrective actions for the hematocrit, $pO_2$, pH, $pCO_2$, Na, K, and Ca sensors and with respect to internal reference solutions A, B, and C are further described below.

Hematocrit

Figure 3C:
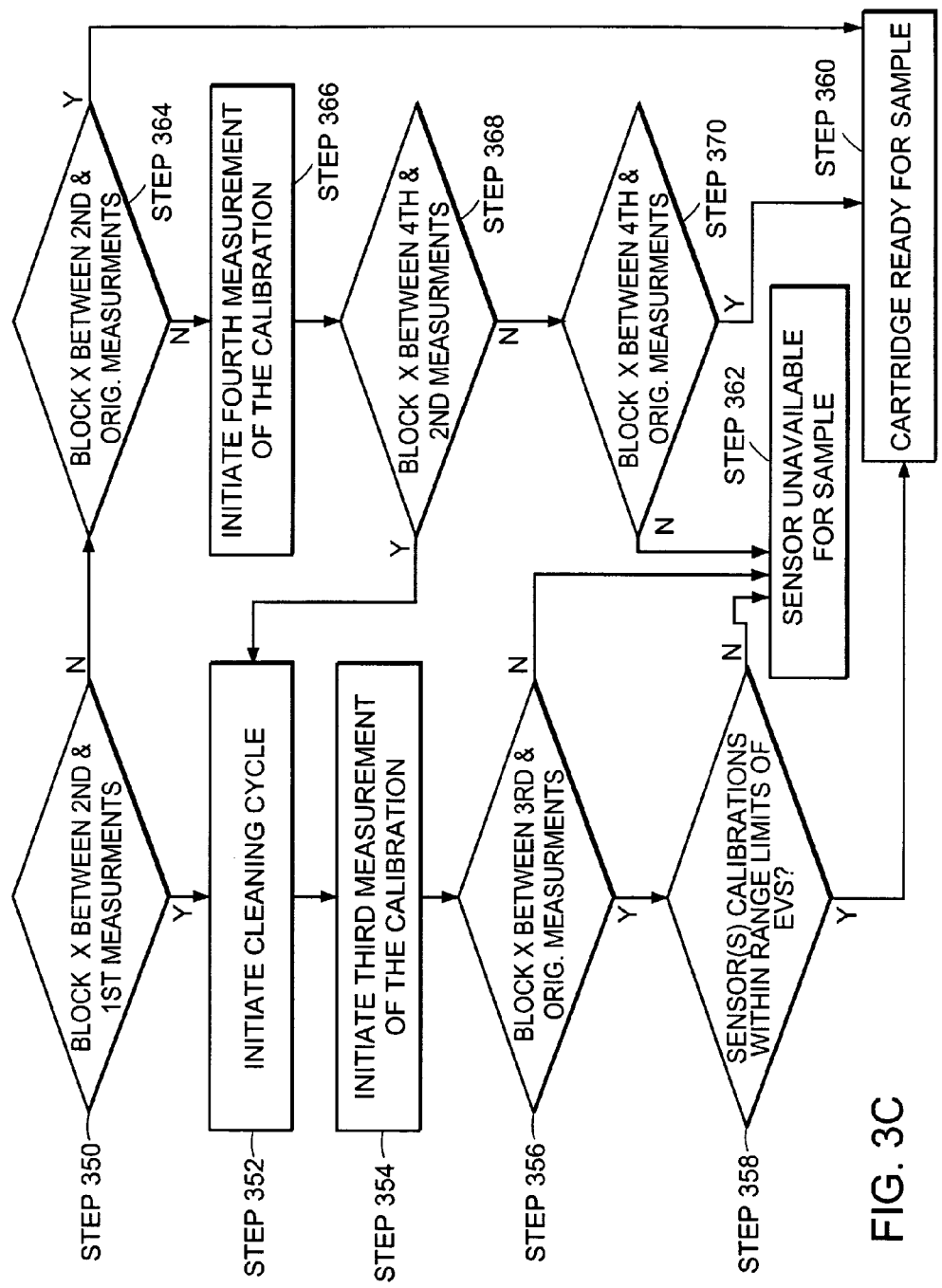

With respect to a hematocrit sensor, the sensor system 8 follows a similar path to that of FIG. 3B. Also referring to FIG. 3C, the sensor system 8 first performs Block X between the second and first measurements of the analyte in STEP 350. If the two drift errors of the two measurements are going in the same direction, the system 8 initiates a cleaning cycle (STEP 352). The system 8 then initiates a third calibration of the measurement (STEP 354) before performing the operations in Block X with respect to the third measurement and the original measurement (STEP 356). If the difference in drift error between the third measurement and the original measurement is in the same direction, the sensor system 8 determines if the sensor calibration is within the range limits of the external verification solution (STEP 358). If the sensor is within the range limits of the EVS (STEP 358), the sensor is ready for sample (STEP 360). If, however, the sensor is outside of the acceptable range limits of the EVS (STEP 358), the sensor is not available for a sample (STEP 362).

If the sensor system 8 determines that the drift errors for the second and first measurements are in different directions (STEP 350), then the sensor system performs the operations in Block X with respect to the second measurement and the original measurement (STEP 364). If the drift error is in the same direction for both measurements, then the system 8 initiates a fourth measurement of the calibration (STEP 366) and then performs the operations of Block X for the fourth measurement and the second measurement of the calibration (STEP 368). If the drift errors are in the same direction, then the sensor system 8 performs the corrective action by initiating a cleaning cycle (STEP 352), as described above. If the drift errors are not in the same direction, then the system 8 performs the operations in Block X with respect to the fourth measurement and the original measurement. If the drift errors are in the same direction, then the cartridge is ready for sample (STEP 360). If not, then the sensor is unavailable for sample (STEP 362).

Failure Patterns and Corrective Actions Related to Internal Reference Solution B Failure patterns have been found to exist for the hematocrit, $pO_2$, pH, $pCO_2$, Na, K, and Ca sensors with respect to the internal reference solution B. The failure patterns include a drift in the concentration with respect to the concentration of the internal reference solution B. The drift value is typically outside of pre-set limits with reference to an original measurement. The failure patterns occur after a sample measurement, and are typically caused by a blood clot on one or more of the sensors.

Referring to FIG. 4A, the electrochemical sensor system 8 first determines if a failure pattern has been detected (STEP 400) with respect to the internal reference solution B. This failure pattern determination can include determining a failure pattern for one or more of the hematocrit sensor, the $pO_2$ sensor, and/or one or more of the pH, $pCO_2$, Na, K, and Ca sensors.

The determination of a failure pattern for the $pO_2$ sensor (STEP 400) preferably includes determining a drift value with respect to the internal reference solution B that is less than a pre-set lower limit with reference to the original measurement. The lower limit for the $pO_2$ sensor can be 12 mmHg less than the original measurement of the $pO_2$ sensor. If no failure pattern with respect to internal reference solution B is detected in STEP 400, then the automatic monitoring and calibration continues (STEP 304) and the sensors are ready for a sample measurement.

The detection of failure patterns for the pH, $pCO_2$, Na, K, and/or Ca sensors (STEP 400) preferably includes detecting drift values with respect to the internal reference solution B that are greater than a pre-set upper limit or less than a pre-set lower limit with reference to the original measurements. In one embodiment, the limits for the pH sensor are ±0.02. The limits for the $pCO_2$ sensor can be ±3 mmHg from the original measurement. Similarly, the limits for the Na sensor can be ±3 mM from the original measurement for a cartridge life greater than 5 hours, and can be −2 mM to +8 mM for a cartridge life less than 5 hours. The limits for the K sensor may be ±0.3 mM from the original measurement. The limits for the Ca sensor may be ±0.06 mM from the original measurement.

In one embodiment, the detection of the failure patterns for the pH, $pCO_2$, Na, K, and Ca sensors (STEP 400) is confirmed by determining whether a reference shift of the internal reference solution B had occurred. In one embodiment, a reference shift is a shift in the concentration of the internal reference solution (e.g., internal reference solution B).

If a reference shift is confirmed in the internal reference solution B, then the failure patterns for the pH, $pCO_2$, Na, K, and Ca sensors are not valid and the sensor returns to automatic monitoring and calibration (STEP 304). If a reference shift is not confirmed in the internal reference solution B, then the failure patterns for the pH, $pCO_2$, Na, K, and Ca sensors are valid.

An occurrence of a reference shift of the reference electrode with respect to internal reference solution B may be determined by numerous methods. In one embodiment according to the invention, the electrochemical sensor system 8 determines a reference shift by calculating the difference in the potential difference (e.g., measured in millivolts) between at least two consecutive measurements of the internal reference solution B by the pH, Na, K, and Ca sensors. In some embodiments, the lowest value of a measurement by the four sensors is subtracted from the highest value of a measurement by the four sensors. The reference value is shifted if the resulting value is less than a predetermined reference value, preferably 0.6 millivolts.

The determination of a failure pattern for the hematocrit sensor (STEP 400) preferably includes, for example, determining a drift value with respect to the internal reference solution B that is greater than a pre-set upper limit with reference to an original measurement. The original measurement, in all cases, refers to the calibration measurement immediately prior to the calibration measurement that exhibits a drift error. The upper limit of a drift value permissible for operation of the hematocrit sensor is from, for example, 1%–10%, preferably 2%, greater than the original measurement of the hematocrit sensor.

Once the failure patterns for the hematocrit, $pO_2$, pH, $pCO_2$, Na, K, and Ca sensors with respect to the internal reference solution B have been detected (STEP 400), a protocol of corrective actions is automatically initiated (STEP 402–STEP 430). The protocol of corrective actions can be accompanied by alerting the user of the sensor error by an alarm such as warning lights on the device turning red and/or an error message being displayed on the control screen.

Referring to FIG. 4A, for instance, if a failure pattern is detected for the hematocrit sensor, the electrochemical sensor system 8 then determines if the failure pattern was only detected in the hematocrit sensor (STEP 402). Referring also to FIG. 4B, if a failure pattern was only detected in the hematocrit sensor, the electrochemical sensor system 8 initiates a rinse protocol (STEP 406) of the sensor. The rinse protocol (STEP 406), for example, includes changing the polarization potential of the glucose and lactate sensors from −0.26 V to −0.46 V, followed by a series of rinses of the sensors with internal reference solution C. The rinse protocol (STEP 406) continues by performing a predetermined number of bubble flush loops (e.g., 10). A bubble flush loop includes the injection of an air bubble into the flow of the rinsing solution as it flows along the sensors. The air bubbles in the rinse provide a type of mechanical scrubbing of the sensors that the flow of rinse solution over the sensors does not provide. The predetermined number of bubble flush loops (e.g., 10) are followed by a predetermined number of rinses (e.g., 3) with internal reference solution B. The rinse protocol (STEP 406) is completed by a re-calibration of the sensors with respect to internal reference solution B and by returning the polarization potential of the glucose and lactate sensors from −0.46 V to −0.26 V.

In one embodiment, the rinse protocol is executed by a rinser. The rinser may be part of the corrective action device, the microprocessor, a separate component or part of any other component in the electrochemical sensor system. The rinser may include a mechanical rinsing mechanism which may be controlled, for instance, via a software program, a hydraulic system, a pneumatic system, and the like. In one embodiment, the rinser includes the peristaltic pump 26 illustrated in FIG. 1.

Following the rinse protocol (STEP 406), the drift of the hematocrit sensor with respect to the internal reference solution B is calculated (STEP 408) from the hematocrit measurement prior to the detection of the failure pattern to the measurement after the rinse. If the drift of the hematocrit sensor is in error of greater than a predetermined threshold (e.g., ±2%) (STEP 410), then the hematocrit sensor fails and is permanently disabled (STEP 412). If the hematocrit drift error is less than ±2%, then a failure pattern is not detected and the hematocrit sensor is ready for use (STEP 414). Following the hematocrit sensor being permanently disabled (STEP 412) or being determined ready for use (STEP 414), the corrective action protocol terminates and all sensors other than the hematocrit sensor are ready for use (STEP 416).

Referring again to FIG. 4A, in the case in which failure patterns for the $pO_2$, pH, $pCO_2$, Na, K, or Ca sensors are detected, the corrective action protocol initiates calibration with respect to the internal reference solution B of only the sensor(s) that exhibited a failure pattern (STEP 418). If a failure pattern is no longer detected following a calibration with respect to the internal reference solution B, then a calibration with respect to the internal reference solution A is initiated (STEP 420).

In one embodiment, if, after the calibration with internal reference solution B (STEP 418), a failure pattern is still detected in any of the sensor(s) exhibiting a previous failure pattern, then a calibration with respect to the internal reference solution B of only the sensor(s) that exhibited a failure pattern is repeated a second time, and, if necessary, a predetermined number of times after the second time, such as one additional time (for a total of three times).

If, after the third calibration (or any predetermined number of calibrations) with respect to the internal reference solution B (STEP 418), a failure pattern is still detected in any of the sensor(s) exhibiting a failure pattern, then a calibration with respect to the internal reference solution A is initiated (STEP 420).

The drift of the $pO_2$, pH, $pCO_2$, Na, K, and Ca sensors with respect to the internal reference solution A is then determined for each sensor from the measurement immediately prior to the detection of the failure pattern and from the measurement immediately after the calibration of the sensor with respect to the internal reference solution A. If the drift of the $pO_2$ sensor with respect to the internal reference solution A is determined to be greater than the pre-set upper limit or is sufficiently in error to be unrecordable in the storage element with reference to the original measurement (STEP 422), then corrective action continues, beginning with a rinse of the sensors (STEP 424) as described in FIG. 4C. Similarly, in one embodiment, if the drift of the pH, $pCO_2$, Na, K, or Ca sensors with respect to the internal reference solution A is determined to be less than the pre-set lower limit with reference to the original measurements (STEP 422), then the corrective action continues with STEP 424 in FIG. 4C. Steps 518–522, as described above, are referred to below as the "Failure Pattern with Internal Reference Solution B Section."

If the drift of the pH, $pCO_2$, Na, K, or Ca sensors with respect to the internal reference solution A is determined to be within the pre-set limits with reference to the original measurements (STEP 422), then the drift error of the Na or Ca sensors with respect to internal reference solutin B is considered (STEP 426) and the presence of a hematocrit failure pattern is considered (STEP 428). If the drift error of the Na or Ca sensors with respect to internal reference solution B is outside the pre-set limits with reference to the original measurements for the sensors (STEP 426) then the user is informed of an interference with the sensor(s) (STEP 430). Thiopental and benzalkonium are two compounds that, if present in the sample, will cause interference. The electrochemical sensor system accepts user acknowledgement of the drift error of the Na or Ca sensors (STEP 424) in order for the sensors to be ready for use and/or the automatic monitoring and calibration of the sensors to begin (STEP 304). If a hematocrit failure pattern is detected (STEP 428), then corrective action continues with the rinse of the sensors (STEP 430) (FIG. 4C). If a hematocrit failure pattern is not detected (STEP 428) then the sensors are ready for use and the automatic monitoring and calibration of the sensors begins (STEP 304). Moreover, steps 526–530 and the previous descriptions relating to these steps are referred to below as "Drift Error Detected Section."

Referring to FIG. 4C, the corrective action for sensors exhibiting a drift error or for when a hematocrit failure pattern is detected continues by performing the rinse protocol (STEP 424), as previously described with respect to STEP 406. The sensor system 8 then executes the Failure Pattern with Internal Reference Solution B Section (STEP 432), as described in FIG. 4A. After executing the Failure Pattern with Internal Reference Solution B Section, the drift of the $pO_2$, pH, $pCO_2$, Na, K, and Ca sensors is determined for each sensor with respect to the internal reference solution A, which was also described above with respect to, for example, STEP 422. If a drift error is not detected, corrective action terminates and the sensors are ready for use (STEP 434). If a drift error is detected, the sensor is permanently disabled for the life of the cartridge (STEP 436). Moreover, the corrective action protocol is terminated and all non-disabled sensors are ready for use (STEP 438).

Failure Patterns and Corrective Actions Related to Internal Reference Solution A In addition to the failure patterns with respect to the internal reference solution B, failure patterns have been found to exist for the $pO_2$, pH, $pCO_2$, Na, K, and Ca sensors with respect to the internal reference solution A. Thus, the failure patterns include a drift error with respect to the internal reference solution A. The failure patterns can occur after a sample measurement in which the drift error is typically caused by a blood clot, and can occur after a calibration with respect to the internal reference solution A.

Referring again to FIG. 4A, the references to the internal reference solution B in the steps and description for FIG. 4A above are swapped with references to the internal reference solution A when determining failure patterns and corrective actions related to internal reference solution A.

For instance, the determination of a failure pattern for the $pO_2$ sensor (STEP 400) preferably includes determining a drift value with respect to the internal reference solution A that is greater than a pre-set upper limit with reference to the original measurements. The upper limit for the $pO_2$ sensor can be, for example, 6 mmHg greater than the original measurement. In one embodiment, the upper limit for the $pO_2$ sensor is between 4–10 mmHg. The failure patterns for the pH, $pCO_2$, Na, K, and Ca sensors include drift values with respect to the internal reference solution A that are less than a pre-set lower limit with reference to the original measurements. The lower limit for the pH sensor can be –0.03 from the original measurement. The lower limit for the $pCO_2$ sensor can be –4 mmHg from the original measurement. The lower limit for the Na sensor can be –3 mM from the original measurement. The lower limit for the K sensor can be –0.2 mM from the original measurement. The lower limit for the Ca sensor can be –0.12 mM from the original measurement. Alternatively, the limits of each sensor may vary with respect to internal reference solution A or internal reference solution B.

Failure Pattern and Corrective Action Related to the $pO_2$ Sensor

A failure pattern specific to the $pO_2$ sensor has been found to exist. This failure pattern occurs infrequently and is not caused by the fouling of the sensor by a sample. The failure pattern for the $pO_2$ sensor includes a drift value with respect to the internal reference solution B that is a predetermined number of times (e.g., 1.5) greater than a pre-set upper limit with reference to the original measurement. The failure pattern also requires that the drift error does not occur during the detection of a different type of failure pattern or during the corrective action initiated by a different type of failure pattern.

The corrective action of the failure pattern initiates a calibration with respect to internal reference solution A. Following the calibration, if the drift of the $pO_2$ sensor is determined to be within the pre-set upper limits of drift with reference to the original measurements then the corrective action is terminated and the sensor is ready for use. If the drift of the $pO_2$ sensor is greater than a pre-set upper limit or is sufficiently in error to be unrecordable, then a second calibration with respect to internal reference solution A is performed. If the drift of the $pO_2$ sensor after the second calibration is within the pre-set limits for drift with reference to the original measurements, then the $pO_2$ sensor is permanently disabled. If, however, the drift of the $pO_2$ sensor after the second calibration is outside the pre-set limits for drift with reference to the original measurements then the corrective action is terminated and the $pO_2$ sensor is ready for use.

Failure Pattern and Corrective Action Related to Detecting Air in the Sensor

A failure pattern related to the detection of air in the sensor channel has been found to exist. The failure pattern is caused by fouling of the sensor by a sample. The fouling causes a short circuit in the hematocrit sensor and thus disabling the sensor's ability to detect whether liquid or air is contacting the sensor. The failure pattern includes two consecutive sensor errors that fail to detect air in the sensor channel. The failure pattern also requires that at least one sample was processed within 2 hours of the first sensor error failing to detect air.

The corrective action protocol initiates the rinse of the sensors. Following the rinse, if the sensor error failing to detect air is eliminated, then the corrective action is terminated and the sensor is ready for use. If, following the rinse, the sensor error failing to detect air is not eliminated, then the user is notified that the sensor function could not be recovered and that the cartridge needs to be replaced.

$pCO_2$ and pH Calibration Confirmation with Internal Reference Solution C

The following three checks have to be performed for $pCO_2$ in a cartridge 37. Failing any of these checks constitutes $pCO_2$ failure and raising the $pCO_2$ flag.

1) Slope Check:

$$pCO_2S=(XCO_2MV+XPHMV)-(CCO_2+CpHMV))/(pHMC-pHB)mV/decade$$

$$pHS=(XpHMV-CpHMV)/(pHMCI-pHB)mV/decade$$

$pCO_2S$ is the pH slope of the $pCO_2$ outer membrane. pHS is the slope of the pH outer membrane. $XCO_2MV$ and XpHMV are the mV values from the last "X" readings for the $pCO_2$ and the pH sensors before the C. $CCO_2MV$ and CpHMV are the mV values from the $pCO_2$ and the pH sensors from the C solution, and pHMCI is the initial measured pH value for the C solution, as described in more detail below. pHB is the pH value for the B solution obtained from the cartridge bar-code. The "B" value shall be used in the above equation if no "X" value is available.

If $pHS-pCO_2S \geq pHSI-pCO_2SI+5$, then the check fails and an internal flag is raised for the $pCO_2$ sensor. In the above equation, "pHSI" and "$pCO_2SI$" are the initial pH slopes of the pH and $pCO_2$ outer membranes obtained from the first cal C after warm-up, as described in more detail below.

2) Threshold Check:

$$PCO2MC=PCO2B*10^{((BPCO2MV-CPCO2MV)/S)} \text{ mmHg}$$

Where PCO2MC is the measured PCO2 value for the C solution, BCO2MV and CPCO2MV are the last B mV readings before the C and the C mV reading, respectively, S is the PCO2 slope from the last 2-point cal, and PCO2B is the PCO2 value for the B solution obtained from the cartridge bar-code.

If PCO2MC−PCO2MCI is outside of the acceptable threshold range specified in section 11, then the PCO2 check fails. In the above equation PCO2MCI is the initial measured PCO2 in the C solution obtained from the first Cal C after warm-up.

3—Drift Check

If PCO2MC−PCO2MC' (PCO2MC is obtain from Threshold Check above and PCO2MC' is the previous PCO2MC) is outside of the acceptable drift range specified in section 11, then before reporting the drift failure another drift check will be performed. In this alternate drift check, the PCO2MC' is replaced with PCO2MC" (PCO2MC" is the measured PCO2 in the C solution prior to PCO2MC'). If this alternate drift check passes, then the check will pass and the alternate check result will be reported. If this alternate drift check fails, then the initial check (using PCO2MC') will be reported. The alternate check is used only when threshold check passes.

pH Buffer Capacity Check During Calibration C

The following two checks have to be performed for pH in iQM cartridges only. Failing either of the two checks will constitute pH failure and raising the pH flag:

1—Threshold Check $$pHMC=(BPHMV-CPHMV)/S+pHB \text{ mmol/L}$$

pHMC is the measured pH value for the C solution, BPHMV is the last B mV readings for the pH before the C, CPHMV is the C mV values from the pH channel, S is the pH slope from the last 2-point cal, and pHB is the pH value for the B solution obtained from the cartridge bar-code.

If PHMC−PHMCI is outside of the acceptable threshold range specified in section 11, then the check fails and an internal flag has to be raised for the pH sensor. In the above equation PHMCI is the initial measured pH in the C solution obtained from the first Cal C after warm-up.

2—Drift Check

If PHMC−PHMC' (PHMC is obtained from Threshold Check above and PHMC' is the previous measured pH in the C solution) is outside of the acceptable drift range specified in section 11, then before reporting the drift failure another drift check will be performed. In this alternate drift check, the PHMC' is replaced with PHMC" (PHMC" is the measured pH in the C solution prior to PHMC'). If this alternate drift check passes, then the check will pass and the alternate check result will be reported. If this alternate drift check fails, then the initial check (using PHMC') will be reported. The alternate check is used only when threshold check passes.

The pH and PCO2 values of the C solution are established during the first Cal C after warm-up. Therefore, the pH/PCO2 checks actually starts with the second Cal C after cartridge warm-up. However, if the pH or PCO2 slope immediately before the first Cal C after warm-up is incalculable, then pH/PCO2 checks will not start until the next Cal C. This logic will apply to subsequent Cal C's until the initial measured values for pH and PCO2 outer membranes are established. The pH and PCO2 values for the C solution are established from the following equations:

$$pHMCI=(BPHIMV-CPHIMV)/pH \text{ slope}+pHB \text{ pH unit}$$

$$PCO2MCI=PCO2B*10^{((BPCO2IMV-CPCO2IMV)/PCO2 \text{ slope})} \text{ mmHg}$$

where BPHIMV and CPHIMV are the pH mV outputs from the B before the C and the first C after warm-up, BPCO2IMV and CPCO2IMV are the PCO2 mV outputs from the B before the C and the first C after warm-up, pH slope and PCO2 slope are the current pH and PCO2 slope values prior to the first C, and pHB and PCO2B are the pH and PCO2 values for the B obtained from the cartridge bar-code.

The initial pH and PCO2 outer membrane slopes are obtained from the first Cal C after cartridge warm-up. These values are calculated form the following equations:

$$PHSI=(XPHIMV-CPHIMV)/(pHMCI-pHB)mV/decade$$

$$PCO2SI=((XPCO2IMV+XPHIMV)-(CPCO2IMV+CPHIMV))/(pHMCI-pHB)mV/decade$$

PHSI and PCO2SI are the initial pH slopes of the pH and PCO2 outer membranes, XPHIMV and XPCO2IMV are the mV values form the last "X" readings for the pH and PCO2 sensors before the first C, and CPHIMV and CPCO2IMV are the mV values from the pH and PCO2 sensors from the first C after warm-up. The "B" value shall be used in the above equations if no "X" value is available.

In one embodiment, the sensor system 8 may maintain and display a corrective action log. Referring to FIG. 5, in one embodiment the sensor system 8 provides a corrective action report 500 regarding the performance and corrective action(s) taken. The corrective action report 500 provides a list of corrective actions taken, such as if the sensor output was adjusted, if the fluidics were checked, and/or if a test needed to be repeated.

Figure 6:
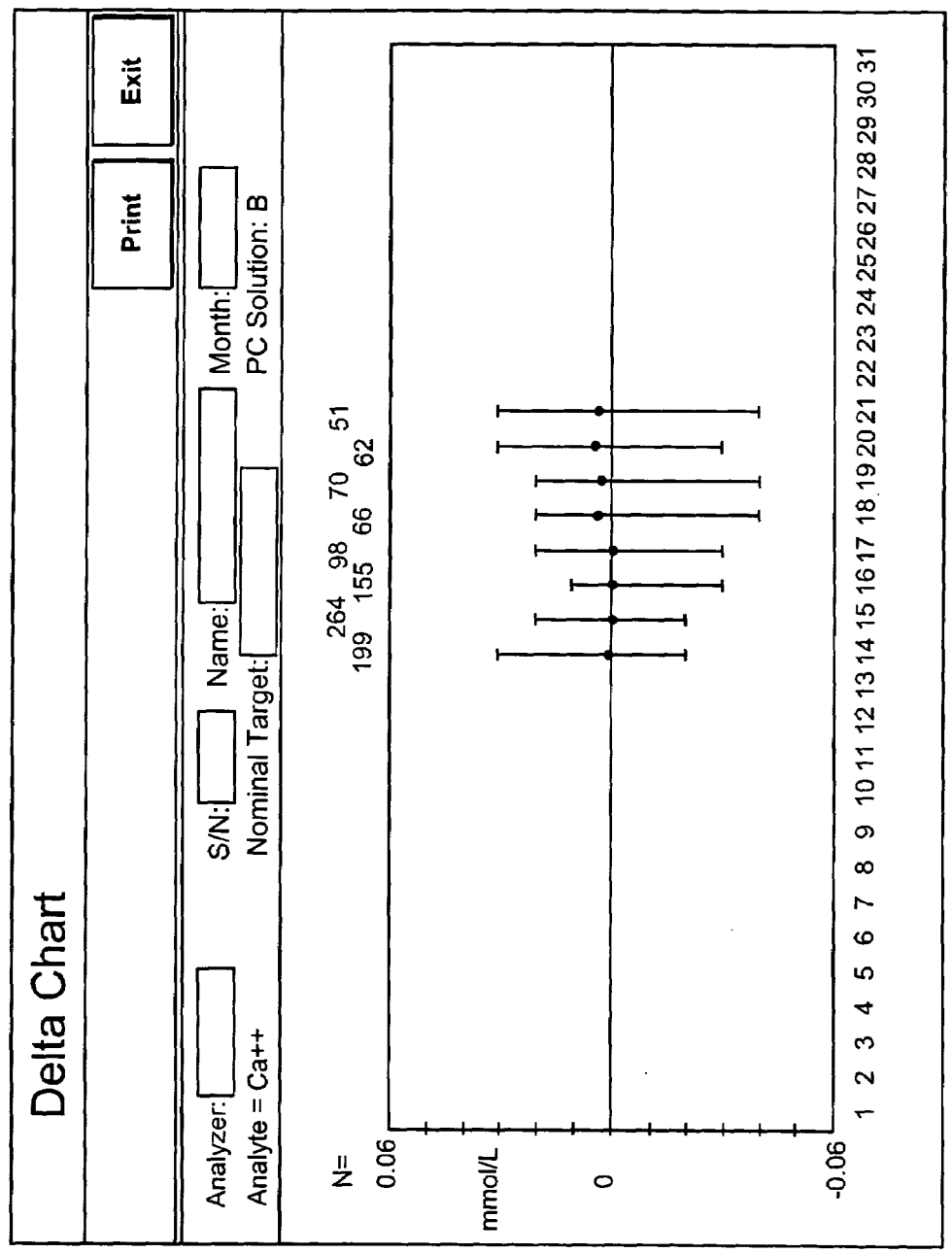
FIG. 6 illustrates an embodiment of a delta chart.

In particular embodiments and referring to FIG. 6, the sensor system 8 may maintain and display a delta chart. These can help determine the accuracy of the sensors and or internal reference solutions. The sensor system 8 may also enable the verification and checking of the electronic components in the system 8, such as verifying the operation of the microprocessor 40 through, for instance, one or more tests. Thus, the sensor system 8 can display, for example, an error log and a delta chart showing drift errors. Further, if the sensor system 8 encounters an error, the system 8 displays an error message. In some embodiments, the error message stays displayed until the user clears the message. In yet other embodiments, the sensor system 8 sounds an alarm when an error occurs.

In other embodiments, the sensor system 8 is a blood glucose monitoring device. The blood glucose device measures a user's blood glucose level from a blood sample applied to a conventional blood testing strip. Although users of a typical blood glucose monitors have to calibrate/check the meter's accuracy by applying an external control solution onto the blood testing strip, the sensor system 8 calibrates and checks the system automatically and internally, without user intervention. An example of a conventional blood glucose monitor includes, but is not limited to, the ONETOUCH devices from LifeScan, Inc.

In other embodiments, the sensor system 8 measures blood urea nitrogen (BUN), which is a metabolic by-product (in the liver) from the breakdown of blood, muscle, and protein. Blood urea nitrogen can be measured from a venipuncture specimen. The sensor system 8 would perform these measurements while not requiring external calibration. In yet another embodiment, the sensor system 8 measures cholesterol, creatine, and the like in the same fashion.

Although the present invention has been described with reference to specific details, it is not intended that such details should be regarded as limitations upon the scope of the invention, except as and to the extent that they are included in the accompanying claims.

What is claimed is:

1. A method for automatic monitoring of a sensor comprising:
   (i) analyzing an analyte comprising a known concentration in a reference solution to determine a first measurement of said known concentration of the analyte in said reference solution;
   (ii) analyzing said analyte in said reference solution to determine a second measurement of said known concentration of said analyte in said reference solution;
   (iii) comparing said known concentration and said first measurement of said analyte;
   (iv) comparing said known concentration and said second measurement of said analyte;
   (v) comparing said first measurement and said second measurement of said analyte; and
   (vi) initiating corrective action if said first measurement of said analyte is substantially similar to said second measurement of said analyte and said first and said second measurements are substantially dissimilar to said known concentration of said analyte.

2. The method of claim 1, wherein said corrective action comprises calibrating said sensor according to said known concentration of said analyte of said reference solution.

3. The method of claim 1, wherein said corrective action comprises rinsing said sensor.

4. The method of claim 1 further comprising the step of providing a sensor system having at least one sensor.

5. The method of claim 4, wherein said sensor system further comprises a sample flow channel disposed adjacent to said sensor.

6. The method of claim 1 wherein the sensor is an electrochemical sensor.

7. The method of claim 1 wherein said reference solution comprises an internal reference solution.

8. The method of claim 7, wherein said sensor is provided in a said cartridge.

9. A method for measuring an analyte in a patient fluid sample comprising automatic monitoring of a sensor system for measuring the analyte concentration in the patient fluid sample, comprising:
   (i) analyzing an analyte comprising a known concentration in a reference solution to determine a first measurement of said known concentration of said analyte;
   (ii) analyzing said analyte in said reference solution to determine a second measurement of said known concentration of said analyte;
   (iii) comparing said known concentration and said first measurement of said analyte;
   (iv) comparing said known concentration and said second measurement of said analyte;
   (v) comparing said first measurement of said analyte and said second measurement of said analyte; and
   (vi) measuring said analyte concentration in said patient fluid sample if said first measurement of said analyte and said second measurement of said analyte are sufficiently dissimilar and said second measurement is sufficiently similar to said known concentration of said reference solution.

10. The method of claim 9 further comprising providing a sensor system having at least one sensor.

11. The method of claim 9 wherein said reference solution comprises an internal reference solution.

12. The method of claim 11 further comprising providing said internal reference solution in a disposable cartridge.

13. The method of claim 9 wherein step (iv) comprises analyzing a blood glucose level of a blood sample.

14. The method of claim 13 further comprising receiving the blood sample from a blood glucose test strip.

15. The method of claim 9 wherein step (iv) comprises analyzing blood urea nitrogen (BUN) concentration of a blood sample.

16. A sensor system comprising:
(a) a reference solution comprising a known concentration of at least one analyte;
(b) a sensor analyzing said analyte to determine a first measurement and a second measurement of said analyte in said reference solution;
(c) a comparator comparing:
   (i) said known concentration and said first measurement;
   (ii) said known concentration and said second measurement; and
   (iii) said first measurement and said second measurement; and
(d) a corrective action device initiating corrective action if said first measurement of said analyte in said reference solution is substantially similar to said second measurement of said analyte in said reference solution and said first and said second measurements are substantially dissimilar to said known concentration of said analyte in said reference solution.

17. The sensor system of claim 16 further comprising a cartridge for holding said internal reference solution.

18. The sensor system of claim 16 further comprising a microprocessor to perform at least one of measurement, calculation, storage, and control functions relating to at least one of said analyte and said measurements of said analyte.

19. The sensor system of claim 18, wherein said microprocessor comprises said corrective action device.

20. The sensor system of claim 16 further comprising a rinser to rinse said sensor.

21. The sensor system or claim 16 wherein the sensor is an electrochemical sensor.

22. A sensor system comprising:
(i) means for analyzing an analyte comprising a known concentration in a reference solution to determine a first measurement of said analyte in said reference solution;
(ii) means for analyzing said analyte in said reference solution to determine a second measurement of said analyte in said reference solution;
(iii) means for comparing said first measurement of said analyte and said second measurement of said analyte in said reference solution;
(iv) means for comparing said first measurement of said analyte and said known concentration of said analyte;
(v) means for comparing said second measurement of said analyte and said known concentration of said analyte; and
(vi) means for initiating corrective action if said first measurement of said analyte is substantially similar to said second measurement of said analyte and said first and said second measurements are substantially dissimilar to said known concentration of said analyte in said internal reference solution.

23. A method for monitoring performance of a sensor for analyzing at least a first and a second patient sample during use life of the sensor, the method comprising the steps of:
(a) verifying the sensor performance during the use life of the sensor only once with an external solution before analyzing a first patient sample; and thereafter
(b) verifying the sensor performance before analyzing the second patient sample using only an internal reference solution to monitor the sensor performance.

24. The method according to claim 23 further comprising in step (a):
(i) initially calibrating the sensor using the internal reference solution; and
(ii) verifying the sensor performance using the external solution.

25. The method according to claim 23 further comprising in step (b):
(i) determining a first measurement by the sensor of a known concentration of an analyte in the internal reference solution;
(ii) determining a second measurement by the sensor of the known concentration of the analyte in the internal reference solution; and
(iii) comparing the known concentration, the first measurement of the analyte, and the second measurement of the analyte to determine sensor performance.

26. The method according to claim 25 further comprising:
(iv) initiating corrective action if the first measurement of the analyte is substantially similar to the second measurement of the analyte and the first and the second measurements are substantially dissimilar to the known concentration of the analyte.

27. The method according to claim 25 further comprising:
(iv) recalibrating the sensor if the first measurement of the analyte is substantially similar to the second measurement of the analyte and the first and the second measurements are substantially dissimilar to the known concentration of the analyte.

28. The method according to claim 25 wherein the sensor is acceptable for analyzing the first sample if the second measurement is dissimilar to the first measurement and the second measurement is substantially similar to the known concentration of the analyte.

29. The method according to claim 25 further comprising:
(iv) recalibrating the sensor with internal reference solution if the first measurement and the second measurement are substantially dissimilar and the first measurement is substantially similar to the known concentration of the analyte.

30. The method according to claim 25 further comprising:
(iv) recalibrating the sensor with the internal reference solution if the first measurement is substantially dissimilar to the second measurement and the first and the second measurements are substantially dissimilar to the known concentration of the analyte.

31. The method according to claim 23 further comprising:
(c) recalibrating the sensor with the internal reference solution if the sensor performance in step (a) or the sensor performance in step (b) is outside a preset range of acceptable sensor performance.

32. The method according to claim 23 further comprising:
(c) initiating corrective action if the sensor performance in step (a) or the sensor performance in step (b) is outside a preset range of acceptable sensor performance.

33. The method according to claim 23 wherein the sensor is an electrochemical sensor.

34. The method according to claim 23 wherein the sensor performance comprises accuracy of the sensor measurement.

* * * * *